United States Patent
Ramakrishnan et al.

(10) Patent No.: US 10,864,091 B2
(45) Date of Patent: Dec. 15, 2020

(54) BIOMIMETIC TRANSFEMORAL KNEE WITH GEAR MESH LOCKING MECHANISM

(71) Applicants: Tyagi Ramakrishnan, White Rock, NM (US); Kyle B. Reed, Tampa, FL (US)

(72) Inventors: Tyagi Ramakrishnan, White Rock, NM (US); Kyle B. Reed, Tampa, FL (US)

(73) Assignee: University of South Florida, Tampa, FL (US)

( * ) Notice: Subject to any disclaimer, the term of this patent is extended or adjusted under 35 U.S.C. 154(b) by 78 days.

(21) Appl. No.: 16/401,886

(22) Filed: May 2, 2019

(65) Prior Publication Data

US 2019/0254843 A1 Aug. 22, 2019

Related U.S. Application Data

(63) Continuation of application No. PCT/US2017/059445, filed on Nov. 1, 2017.
(Continued)

(51) Int. Cl.
*A61F 2/64* (2006.01)
*A61F 2/68* (2006.01)
*A61F 2/50* (2006.01)

(52) U.S. Cl.
CPC .............. *A61F 2/644* (2013.01); *A61F 2/642* (2013.01); *A61F 2/68* (2013.01);
(Continued)

(58) Field of Classification Search
CPC .. A61F 2/644; A61F 2/64; A61F 2/642; A61F 2002/30523; A61F 2002/5072;
(Continued)

(56) References Cited

U.S. PATENT DOCUMENTS

| 47,353 A | 4/1865 | Burr |
|---|---|---|
| 50,770 A | 10/1865 | Lockwood |

(Continued)

FOREIGN PATENT DOCUMENTS

| AT | 212973 | 1/1961 |
|---|---|---|
| WO | 9624312 A1 | 8/1996 |

(Continued)

OTHER PUBLICATIONS

Boyce, Meherwan P. Gas turbine engineering handbook. Chapter 14, "Gears," pp. 605-625. Elsevier, 2011. (Year: 2011).*

(Continued)

*Primary Examiner* — Brian A Dukert
*Assistant Examiner* — Amanda M Barkan
(74) *Attorney, Agent, or Firm* — Smith & Hopen, P.A.; Paul Murty

(57) ABSTRACT

A prosthetic knee having a passive knee locking mechanism that uses the same four-bar mechanics found in a natural knee. The flexible four-bar mechanism guides the motion of the knee, aids in the return of the knee from full flexion to extension, and connects a femoral gear to a tibial gear. The gears have a circular radius and are connected using parallel links to keep the femur and tibia together when the knee is active. The knee stays locked throughout the stance phase. At toe off, no weight is applied on the prosthetic knee allowing the knee to flex. The flexible links are stretched, thereby increasing the stiffness in the springs, and at terminal swing phase, moments before heel strike, the flexible links in the four-bar mechanism snap back to the extended/locking position and lockout once the user applies his/her weight on the knee.

17 Claims, 18 Drawing Sheets

Related U.S. Application Data

(60) Provisional application No. 62/416,479, filed on Nov. 2, 2016.

(52) U.S. Cl.
CPC . *A61F 2002/503* (2013.01); *A61F 2002/5007* (2013.01); *A61F 2002/5009* (2013.01); *A61F 2002/5043* (2013.01); *A61F 2002/5073* (2013.01); *A61F 2002/6836* (2013.01); *A61F 2002/6854* (2013.01)

(58) Field of Classification Search
CPC ...... A61F 2002/5007; A61F 2002/5009; A61F 2002/5075; A61F 2002/5093; A61F 2002/5043; A61F 2002/30528; A61F 2002/6836; A61F 2005/0139; A61F 5/00; A61F 5/01; A61F 5/042; B25J 9/0006; A61H 3/00

See application file for complete search history.

(56) References Cited

U.S. PATENT DOCUMENTS

| | | | |
|---|---|---|---|
| 3,779,654 A | | 12/1973 | Horne |
| 3,969,773 A | | 7/1976 | Menschik |
| 4,090,264 A | | 5/1978 | Thompson |
| 5,246,465 A | | 9/1993 | Rincoe et al. |
| 6,527,733 B1 | * | 3/2003 | Ceriani ............... A61F 5/0123 602/16 |
| 2007/0106191 A1 | | 5/2007 | Mueller et al. |
| 2008/0119931 A1 | | 5/2008 | Fell et al. |
| 2008/0269913 A1 | | 10/2008 | Gobbers et al. |
| 2009/0177282 A1 | | 7/2009 | Bureau et al. |
| 2014/0052265 A1 | * | 2/2014 | Slocum, Jr. ............ A61F 2/384 623/20.24 |
| 2014/0188252 A1 | * | 7/2014 | Sadler ..................... A61F 2/644 623/46 |
| 2016/0015531 A1 | * | 1/2016 | Cheng ...................... A61F 2/64 623/39 |
| 2017/0119569 A1 | * | 5/2017 | Hsu ....................... A61F 5/0123 |

FOREIGN PATENT DOCUMENTS

| | | |
|---|---|---|
| WO | 2012177125 A1 | 12/2012 |
| WO | 2013060742 A1 | 5/2013 |
| WO | 2015169934 A1 | 11/2015 |

OTHER PUBLICATIONS

Andriacchi et al., The influence of total knee-replacement design on walking and stair-climbing. Journal of Bone and Joint Surgery. 1982. vol. 64-A (No. 9): 1328-1335.

Goldfarb et al., Realizing the promise of robotic leg prostheses. Science translational medicine. 2013. vol. 5 (Issue 210): 210ps15.

Jin et al., Kinematic and dynamic performance of prosthetic knee joint using six-bar mechanism. Journal of rehabilitation research and development. 2003. vol. 40 (No. 1): 39-48.

Kark et al., Patient satisfaction following lower-limb amputation: the role of gait deviation. Prosthetics and orthotics international. 2011. vol. 35 (No. 2): 225-233.

Mcgibbon. A biomechanical model for encoding joint dynamics: applications to transfemoral prosthesis control. Journal of Applied Physiology. 2012. vol. 112: 1600-1611.

Narang. Identification of design requirements for a high-performance, low-cost, passive prosthetic knee through user analysis and dynamic simulation. Doctoral dissertation, Massachusetts Institute of Technology. 2013. 1-98.

Radcliffe. Four-bar linkage prosthetic knee mechanisms: kinematics, alignment and prescription criteria. Prosthetics and orthotics international. 1994. vol. 18: 159-173.

Ramakrishnan et al., Biomimetic transfemoral knee with gear mesh locking mechanism. International Journal of Engineering Research & Innovation. 2016. vol. 8 (No. 2): 30-38.

Ramakrishnan et al. Combined Gait Asymmetry Metric. 38th Annual International Conference of the IEEE Engineering in Medicine and Biology Society (EMBC). 2016. 2165-2168.

Silver-Thorn et al., Functional stability of transfemoral amputee gait using the 3r80 and total knee 2000 prosthetic knee unit. JPO: Journal of Prosthetics and Orthotics. 2009. vol. 21 (No. 1): 18-31.

Sup et al., Design and control of a powered transfemoral prosthesis. The International journal of robotics research. 2008. vol. 27 (No. 2): 263-273.

Sup et al., Self-contained powered knee and ankle prosthesis: Initial evaluation on a transfemoral amputee. 2009 IEEE International Conference on Rehabilitation Robotics. IEEE. 2009: 638-644.

Winter. The biomechanics and motor control of human gait. University of Waterloo Press. 1998: 1-80.

Translation of Austrian Patent AT212973B dated Jan. 10, 1961; Applicant: Fritz Krapinger.

Translation of International Application Publication No. WO 20131060742 A1 published on May 2 2013; Applicant: Fraunhofer-Gesellschaft Zur Förderung Der Angewandten Forschung.

Translation of International Application Publication No. WO 2015/169934 A1 published on Nov. 12, 2015; Applicant: Fraunhofer-Gesellschaft Zur Förderung Der Angewandten Forschung E.V.

International Search Report and Written Opinion for PCT/US2017/059445 (filing date: Nov. 1, 2017) dated Jan. 23, 2018; Applicant: University of South Florida.

International Preliminary Report on Patentability for PCT/US2017/059445 (filing date: Nov. 1, 2017) with a priority date of Nov. 2, 2016; Applicant: Ramakrishnan, Tyagi et al.

\* cited by examiner

BIOMIMETIC TRANSFEMORAL KNEE WITH GEAR MESH LOCKING MECHANISM

CROSS-REFERENCE TO RELATED APPLICATIONS

This application is a continuation of and claims priority to International Patent Application No. PCT/US2017/059445, entitled "BIOMIMETIC TRANSFEMORAL KNEE WITH GEAR MESH LOCKING MECHANISM", filed Nov. 1, 2017 by the same inventors, which claims priority to U.S. Provisional Patent Application No. 62/416,479, entitled "Biomimetic Transfemoral Knee with Gear Mesh Locking Mechanism", filed Nov. 2, 2016 by the same inventors, the entirety of which is incorporated herein by reference.

FEDERALLY SPONSORED RESEARCH OR DEVELOPMENT

This invention was made with Government support under Grant No. MRI-1229561 awarded by the National Science Foundation. The government has certain rights in the invention.

BACKGROUND OF THE INVENTION

1. Field of the Invention

This invention relates, generally, to prostheses. More specifically, it relates to a prosthetic knee joint.

2. Brief Description of the Prior Art

The human gait consists of a synchronized and cyclic movement of each leg that helps a person move forward [Perry, J., et al. (1992). Gait analysis: normal and pathological function]. Gait is a complex and coordinated process that recruits a range of muscles to actuate the motion. This coordination is disrupted by a limb amputation. The knee and ankle joints are a vital part of human locomotion. They are responsible for articulation, load bearing, and the general dynamic control of overall stable gait [Morrison, J. B. (1970). The mechanics of the knee joint in relation to normal walking. Journal of biomechanics, 3(1), 51-61]. Therefore, amputation that causes a loss of either joint is detrimental to a person's gait [Highsmith, M. J., e al. (2010). Safety, energy efficiency, and cost efficacy of the C-Leg for transfemoral amputees: A review of the literature. Prosthetics and orthotics international, 34(4), 362-377]. Improving the design of prostheses can greatly increase the quality of life of a person with an amputation by increasing their potential mobility. The knee joints are especially vital to a successful transition to a stable gait. There are about seven million trans-femoral amputees across the world [Sup, F., et al. (2009, June). Self-contained powered knee and ankle prosthesis: Initial evaluation on a transfemoral amputee. In 2009 IEEE International Conference on Rehabilitation Robotics (pp. 638-644). IEEE], and each amputee is unique and hence, requires a custom prosthesis. With the advent of 3D printing technology on the rise, it is becoming possible to customize a prosthesis to a specific individual's size and gait pattern [Sup, F., et al. (2008). Design and control of a powered transfemoral prosthesis. The International journal of robotics research, 27(2), 263-273]. It is becoming possible to tailor make a prosthesis that is anatomically similar to the person while making the design inexpensive and passive.

Specifically, 3D printing in prosthetics is a recent development that has been successfully implemented in making cheap prosthetic hands for children [J. Zuniga, et al., "Cyborg beast: a low-cost 3d-printed prosthetic hand for children with upper-limb differences," BMC research notes, vol. 8, no. 1, p. 10, 2015]. This is a logical step for incremental development because a child's arm does not have to take up excessive loads (as a prosthetic knee would) that will be constantly taking up loads that are equivalent to the user's body weight or more depending on the tasks. This enables 3D printed arms to be made of cheaper materials, such as acrylonitrile butadiene styrene (ABS) and polylactide (PLA).

Lower limb prosthetics were developed starting with custom made sockets [N. Herbert, et al., "A preliminary investigation into the development of 3-d printing of prosthetic sockets," Journal of rehabilitation research and development, vol. 42, no. 2, p. 141, 2005] and implants for knee replacement [J. He, et al., "Custom fabrication of a composite hemi-knee joint based on rapid prototyping," Rapid prototyping journal, vol. 12, no. 4, pp. 198-205, 2006]. The socket designs are improved because the 3D point cloud from scans can be used to develop a custom profile for the prosthetic socket. This improves fit and comfort for the amputee. Researchers have also demonstrated that the sockets can have embedded sensors that can monitor the residual limb's condition [D. M. Sengeh et al., "A variable-impedance prosthetic socket for a trans-tibial amputee designed from magnetic resonance imaging data," JPO: Journal of Prosthetics and Orthotics, vol. 25, no. 3, pp. 129-137, 2013]. Similarly, for knee replacement, endo prosthetic development using 3D printing can be used to make molds for casting titanium components that can then be implanted into the patient.

The human knee is a versatile and complex joint. It is a condylar joint formed at the interface of the distal femur and the proximal tibia bones. The knee is controlled by several femoral and tibial muscles that help in the joint's nuanced control and weight bearing. From the sagittal plane, the knee joint flexion involves rotation and anterior translation of the femoral condyle over the proximal tibial surface. The knee also utilizes the Anterior and Posterior Cruciate ligaments that form integral physical parts in the performance of the human knee. Alterations such as reconstruction of the ligaments, that may be due to injuries, result in a dramatic change in the person's gait [R. Ferber, et al., "Gait mechanics in chronic acl deficiency and subsequent repair," Clinical biomechanics, vol. 17, no. 4, pp. 274-285, 2002]. This is amplified if a person undergoes transfemoral amputation and loses the knee and ankle joint. Designing better prosthetics is then vital to restore an amputee's gait quality and function.

Specifically, the ACL and PCL, which play an integral part of knee kinematics are modelled as a cross linked four-bar mechanism [Ponce-Saldias, et al. (2015). Relevance of the hyperelastic behavior of cruciate ligaments in the modeling of the human knee joint in sagittal plane. Revista Facultad de Ingeniería Universidad de Antioquia, (76), 123-133; U.S. Pat. No. 6,749,640; Etoundi, A. C., et al. (2013). A Bio-Inspired Condylar Hinge for Robotic Limbs. Journal of Mechanisms and Robotics, 5(3), 031011; Zavatsky, A. B., et al. (1992). A Model of human knee ligaments in the sagittal plane: part 1: response to passive flexion. Proceedings of the Institution of Mechanical Engineers, Part H: Journal of Engineering in Medicine, 206(3), 125-134], shown in FIG. 1. Anatomically, the mechanism consists of the femur, tibia, ACL, and PCL. The simplistic representation as a four-bar mechanism excludes the fact that the knee joint is controlled by several muscles to execute refined motion [Hamon, A., et al. (2014). Two walking gaits for a planar bipedal robot equipped with a four-bar mechanism for the knee joint. Multibody System Dynamics, 31(3), 283-307]. The knee joint rolls and slides as it goes from extension to flexion, which is called knee roll back [Massin, P., et al. (2006). Optimization of the posterior condylar offset, tibial slope, and condylar roll-back in total knee arthroplasty. The Journal of arthroplasty, 21(6), 889-896]. This motion is controlled by the ACL and PCL that stabilize the knee at every position. A tear in either ligament causes detrimental effects to the motion of the knee, which in turn greatly affects a person's gait [Lewek, M., et al. (2002). The effect of insufficient quadriceps strength on gait after anterior cruciate ligament reconstruction. Clinical Biomechanics, 17(1), 56-63].

The knee can be closely represented by a polycentric mechanism. Polycentric mechanisms are one of the five forms of passive knee mechanisms: manual, single axis, weight activated, and knee with exterior hinges [Radcliffe, C. W. (1994). Four-bar linkage prosthetic knee mechanisms: kinematics, alignment and prescription criteria. Prosthetics and orthotics international, 18(3), 159-173; Michael, J. W. (1999). Modern prosthetic knee mechanisms. Clinical orthopaedics and related research, 361, 39-47]. The knees are designed to assist amputees with various control levels given by the K level (K is an arbitrary letter assigned by HCFA) [Id.]. Low control amputees of the scale K0-K2 rely on manual locking mechanisms. The manual locking knee relies on user input to lock and unlock the knee joint during gait, thereby giving full control to the user. The widely used polycentric knees are for user with medium to high control [Mukul, P., et al. (2010, May). Stanford-Jaipur knee joint for transfemoral amputees. In Proceedings of the 13th world congress of the International Society for Prosthetics and Orthotics (pp. 1179-80)]. A 4, 5, or 6 bar mechanisms [Radcliffe, C. W. (1994). Four-bar linkage prosthetic knee mechanisms: kinematics, alignment and prescription criteria. Prosthetics and orthotics international, 18(3), 159-173; Jin, D., et al. (2003). Kinematic and dynamic performance of prosthetic knee joint using six-bar mechanism. Journal of rehabilitation research and development, 40(1), 39]. Kinematic and dynamic performance of prosthetic knee joint using six-bar mechanism. Journal of rehabilitation research and development, 40(1), 39] can be used for a polycentric knee. These mechanisms shift the instantaneous center at different point of the gait cycle to improve locking and unlocking of the knee joint. Other mechanisms such as single axis are used in conjunction with hydraulic systems or weight activated locking to aid in control and return to extension [Michael, J. W. (1999). Modern prosthetic knee mechanisms. Clinical orthopaedics and related research, 361, 39-47].

There have been several attempts to recreate the human knee joint in a prosthetic mechanism. Design of prosthetic knees falls into one of two categories: endo and exo. Endo-prosthetic knees are biomimetic and follow the contours of the femoral condyles and the tibial surface [T. Andriacchi, et al., "The influence of total knee-replacement design on walking and stair-climbing," Journal of Bone and Joint Surgery-Series A, vol. 64, no. 9, pp. 1328-1335, 1982]. They are usually surgically implanted onto patients during total knee replacements.

Exo-prosthetic knees are fitted on amputees and are disposed outside the body cavity. These exo-prosthetic knees can be further classified into active and passive mechanisms [M. Cantos, "Pirates & peg legs: A historical look at amputation and prosthetics," History of Medicine Days, vol. 14, pp. 16-20, March 2005; D. S. Childress, "Historical aspects of powered limb prostheses," Clinical prosthetics and orthotics, pp. 2-13, 1985]. Active knee mechanisms are considered state of the art and the designs incorporate complex mechanisms that enable the actuators to mimic human walking [Sup, F., et al. (2008). Design and control of a powered transfemoral prosthesis. The International journal of robotics research, 27(2), 263-273]. Active knee mechanisms cause lower metabolic strain than passive knees in tasks such as walking, stair ascent, traversing slopes, and ambulatory tasks [Highsmith, M. J., e al. (2010). Safety, energy efficiency, and cost efficacy of the C-Leg for transfemoral amputees: A review of the literature. Prosthetics and orthotics international, 34(4), 362-377; Highsmith, M. J., et al. (2011). Kinetic asymmetry in transfemoral amputees while performing sit to stand and stand to sit movements. Gait & posture, 34(1), 86-91; Boonstra, A. M., et al. (1995). Energy cost during ambulation in transfemoral amputees: a knee joint with a mechanical swing phase control vs a knee joint with a pneumatic swing phase control. Scandinavian journal of rehabilitation medicine, 27, 77-77]. Active knees use variable control algorithms to adjust for the terrain and environmental conditions.

While active knees show tremendous potential in the knee's ability to adapt to different walking speeds and better replicate the normal gait, designs are just beginning to enter the market [J. L. Johansson, et al., "A clinical comparison of variable-damping and mechanically passive prosthetic knee devices," American journal of physical medicine & rehabilitation, vol. 84, no. 8, pp. 563-575, 2005]. Active knees remain expensive, difficult to prescribe, and require extensive training for proper fitting and tuning [Goldfarb, M., et al. (2013). Realizing the promise of robotic leg prostheses. Science translational medicine, 5(210), 210ps15-210ps15]. Currently, they are more intended for transfemoral amputees who require more control from their prosthesis. Indeed, transfemoral amputees usually use their passive knee prostheses more than active knee prostheses [Narang, Y. S. (2013). Identification of design requirements for a high-performance, low-cost, passive prosthetic knee through user analysis and dynamic simulation (Doctoral dissertation, Massachusetts Institute of Technology)].

There are various options of passive knee prosthetics available for amputees with control level classifications from K0 to K4. Single-axis knees allow for limited movement but provide greater assistance and are sometimes ideal for transfemoral amputees who have lower levels of control (K0-K2). Another popular choice is the polyaxial knee with multiple centers of rotation and is often based on a four-bar mechanism [C. Radcliffe, "Four-bar linkage prosthetic knee mechanisms: kinematics, alignment and prescription criteria," Prosthetics and orthotics international, vol. 18, no. 3, pp. 159-173, 1994; P. Mukul, et al., "Stanford-jaipur knee joint for trans femoral amputees," in Proceedings of the 13th world congress of the International Society for Prosthetics and Orthotics, Leipzig, Germany, 2010, pp. 10-15; D. Jin, et al., "Kinematic and dynamic performance of prosthetic knee joint using six-bar mechanism," Journal of rehabilitation research and development, vol. 40, no. 1, pp. 39-48, 2003].

The Ossur Total Knee [U.S. Pat. No. 8,764,849] is an example of a common polyaxial mechanism and is used as a comparison in this specification. It makes use of hydraulics to adapt to different walking speeds. At longer strides, the hydraulic system provides more resistance to excess flexion and uses that built up energy to assist in the forward swing on the prosthetic leg [M. B. Silver-Thorn et al., "Functional stability of transfemoral amputee gait using the 3r80 and total knee 2000 prosthetic knee units," JPO: Journal of Prosthetics and Orthotics, vol. 21, no. 1, pp. 18-31, 2009]. The hydraulic design has become typical in better prosthetics that allow for a greater variety of movement and provide for a more human-like gait. However, hydraulic knees remain heavy, costly, and difficult to personalize, and they require extensive maintenance.

There is also a necessity for prosthetics to be unique to every amputee's condition. Current prosthetic products are designed to be of similar dimensions due to manufacturing, design, and cost constraints. Fitting prosthetics that are not suitable to the user's dimensions causes an array of problems with their gait dynamics which in turn leads to physical pain to the amputee.

What is needed is a prosthetic knee joint has a four-bar mechanism to mimic the natural four-bar mechanics found in the knee joint. The natural four-bar mechanics are comprised of the distal end of the femur, the proximal end of the tibia, the ACL, and the PCL. Movement about a more posterior axis allows for greater control and gives rise to greater stability in mechanisms that lock in a load bearing stance.

Current prosthetic knee designs fail to provide a natural four-bar mechanism that includes a spring force to aid in extension and flexion similar to a natural human knee joint. For example, U.S. Pat. No. 6,749,640 B1 to Luhrs et al. discloses a four-bar mechanism with each bar having a rigid construction incapable of providing a spring force to aid in the flexion and extension of the knee joint. U.S. Pat. No. 4,090,264 to Thompson similarly fails to include a natural four-bar mechanism having linkages between the prosthetic tibia and the prosthetic femur that have spring forces to aid in extension and flexion similar to a natural human knee joint.

U.S. Pat. No. 5,246,465 to Rincoe et al. is an active and complex system relying on cables and motors to actuate the knee mechanism through a worm gear drive. Active systems tend to be heavy and have slower times for flexion and extension. In contrast, the current invention is completely passive and the amount of flexion and extension are controlled by spring stiffness of the links that act as the ACL and PCL of the human knee. Moreover, the current invention does not require a housing to mount all the parts. The assembly is open and helps to reduce the weight of the design.

Accordingly, what is needed is a passive prosthetic knee joint designed to provide a more natural motion using a four-bar mechanism with linkages between the prosthetic tibia and the prosthetic femur that have spring forces to aid in extension and flexion. However, in view of the art considered as a whole at the time the current invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The current invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved transfemoral prosthesis, and knee component thereof, is now met by a new, useful, and nonobvious invention.

In an embodiment, the current invention is a passive transfemoral prosthesis or a biomimetic, prosthetic knee apparatus thereof. The transfemoral prosthesis includes a prosthetic femur, a prosthetic shank/tibia, a prosthetic foot assembly, and the prosthetic knee apparatus. On its top end, the prosthetic femur is coupled to a residual or impaired limb connector (e.g., via a titanium pyramid head). The prosthetic shank is passive and rotatable relative to the prosthetic femur. The foot assembly is disposed in underlying relation to the prosthetic shank and is coupled thereto (e.g., via a bolt connector).

The prosthetic knee apparatus is disposed between the prosthetic femur and the prosthetic tibia. The knee apparatus includes a femoral gear and a tibial gear. The femoral gear has a curved posterior side with an array of femoral teeth disposed along a bottom side and the posterior side of the femoral gear. Similarly, the tibial gear has a curved posterior side with an array of tibial teeth disposed along a top side and the posterior side of the tibial gear. The femoral gear is disposed in substantially overlying relation to the tibial gear when the gears are in an upright position (e.g., when the user is standing straight up). The femoral and tibial teeth (e.g., pressure angle of about 14.5°) engage in a meshable relationship with each other. The curved sides of the femoral and tibial gears mirror each other across a horizontal plane therebetween, such that the gears are posteriorly rotatable relative to each other along their curved sides with their teeth meshing as the gears rotate relative to each other. Optionally, the femoral and tibial gears can have a substantially semi-circular shape with linear portions that mesh with each other in the upright position and curved portions that mesh with each other during rotation of the gears.

The knee apparatus further includes an anterior hard-stop that prevents anterior rotation of the gears when the gears are in the upright position. The hard-stop may include an anterior femoral stop extending downwardly along the femoral gear and an anterior tibial stop extending upwardly along the tibial gear. The femoral stop prevents anterior rotation of the tibial gear when the femoral stop and the tibial stop abut each other, which occurs in the upright position.

The ligament links have an end secured to the femoral gear and an opposite end secured to the tibial gear. The links further have a biased force that facilitates posterior-anterior rotation of the gears relative to each other. Additionally, the links function as stabilizers in order to make sure that the knee is in full extension and stays locked while the amputee shifts weight on to the prosthetic. The ligament links may include an ACL link and a PCL link. The ACL link is secured to the femoral gear in a posterior position and secured to the tibial gear in an anterior position, such that the ACL link extends in a posterior-to-anterior direction in the upright position of the gears. The PCL link is secured to the femoral gear in an anterior position and secured to the tibial gear in a posterior position, such that the PCL link extends in an anterior-to-posterior direction in the upright position of the gears.

In certain embodiments, the femoral and tibial gears each include two sets of teeth positioned on lateral sides of the knee apparatus. Corresponding femoral and tibial teeth on the lateral sides of the knee apparatus mesh with each other, defining an open space therebetween. In further embodiments, the ligament links can operate as a cross-linked four-bar spring mechanism that mimics an ACL and a PCL of a healthy knee. More specifically, the ligament links includes two ACL links and two PCL links, where the links are structured similar to the ones previously discussed. The first ACL link is disposed on a lateral outer surface of one set of corresponding gear teeth, and the first PCL link is disposed on a lateral inner surface of this set of gear teeth. The second ACL link is disposed on a lateral inner surface of the opposite set of corresponding gear teeth, and the second PCL link is disposed on a lateral outer surface of this set of gear teeth. These links may be provided on the sides, as described here, to prevent lateral slippage.

In a separate embodiment, the current invention is a passive transfemoral prosthesis or a biomimetic, prosthetic knee apparatus thereof, where the prosthesis or knee apparatus include any one or more—or even all—of the foregoing characteristics and functions.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
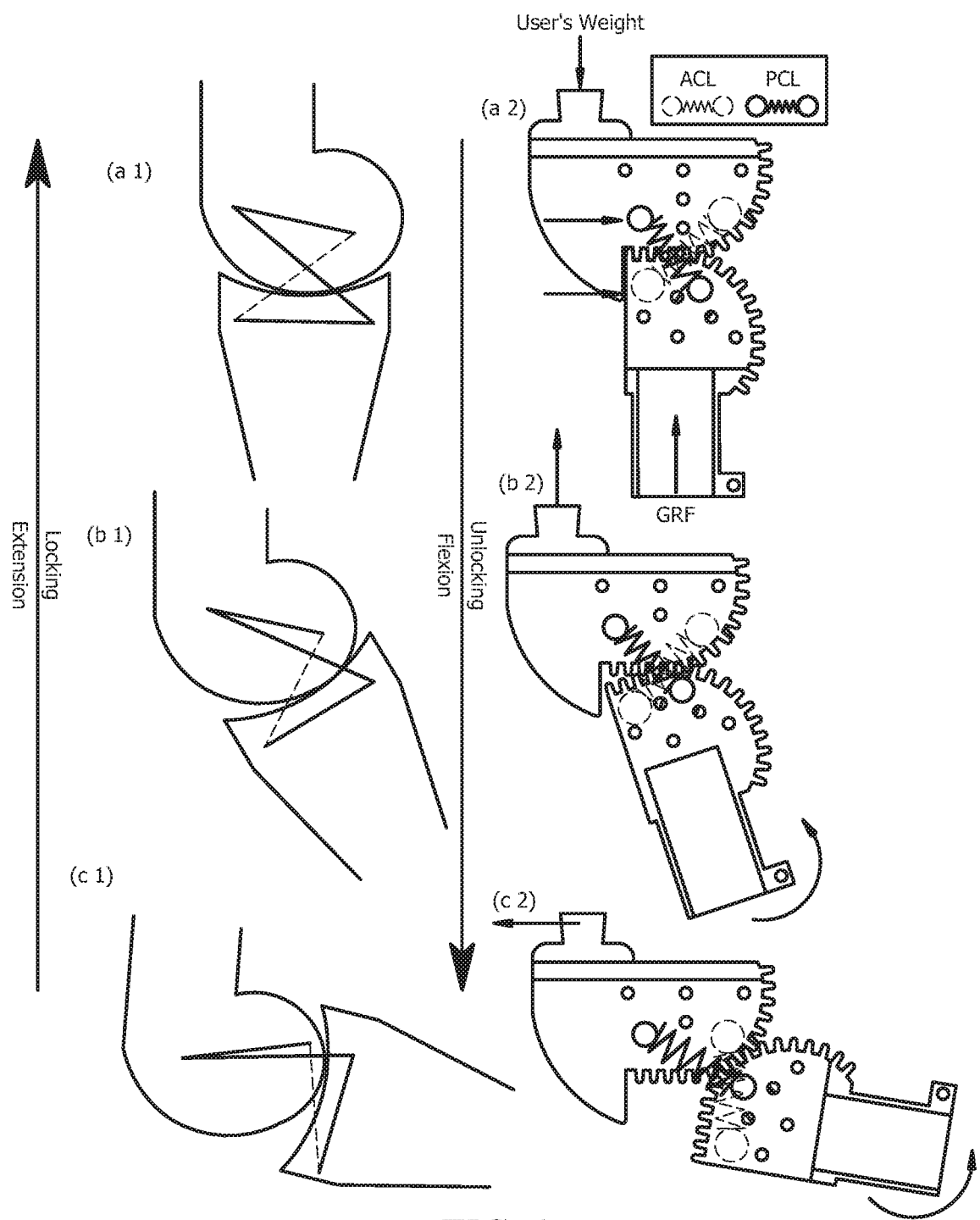
FIG. 1 depicts the typical motion of the human knee versus the motion of the current invention. Specifically, (a 1) is a side view of a locked setting of the knee where the user's weight and ground reaction forces (GRF) are acting on the knee, (a 2) is a cross sectional view of an embodiment of the current invention where the ACL and PCL springs are in a lockout position, (b 1) is a side view of a knee at terminal swing just before heel strike, (b 2) is a cross sectional view of terminal swing of an embodiment of the current invention showing the spring arrangement, (c 1) is an unlocked knee at full flexion, and (c 2) is a cross sectional view of an embodiment of the current invention showing the spring arrangement.
Figure 2:
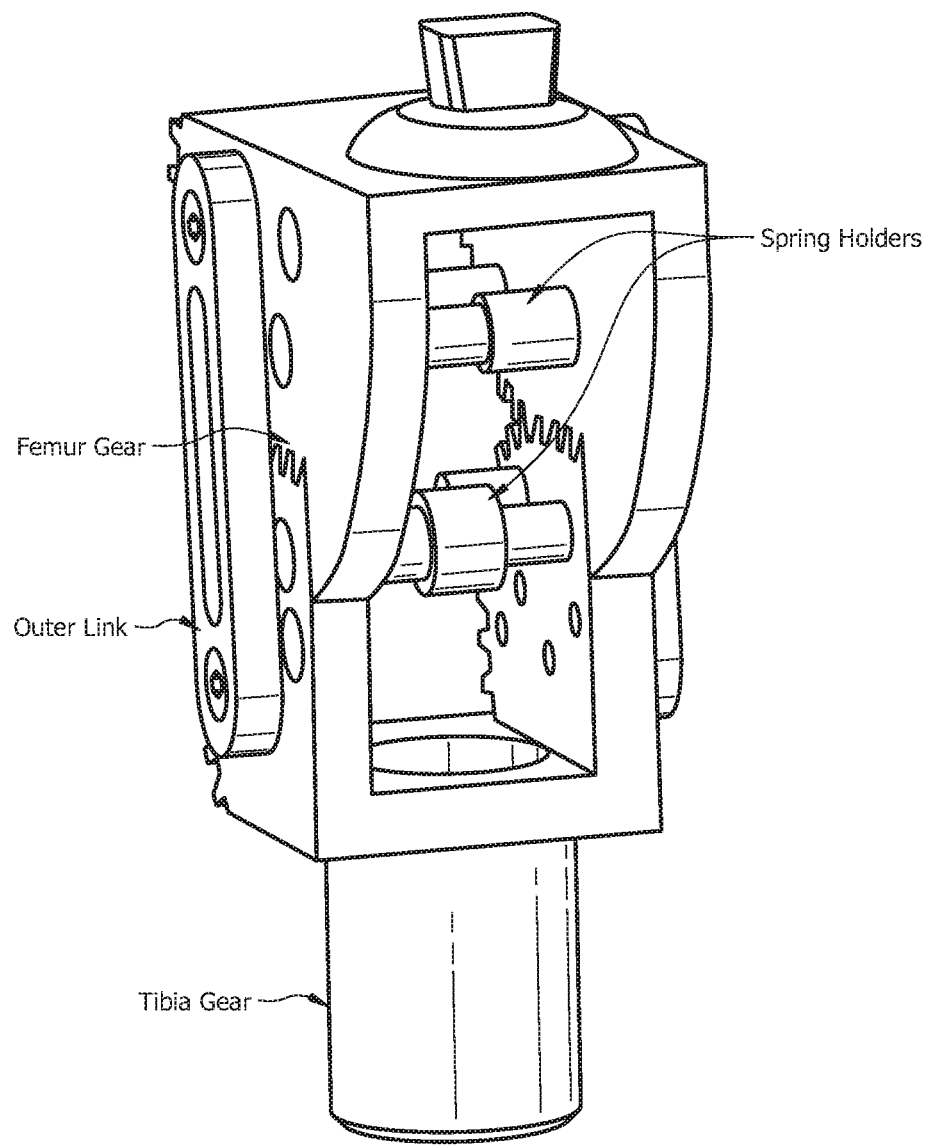
FIG. 2 is a front perspective view of an embodiment of the current invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

It is an object of certain embodiments of the current invention to provide an anatomically-scalable transfemoral prosthetic knee that can be 3D printed using carbon fiber and nylon composite. The prosthetic knee is designed to have a polyaxial cross-linked spring mechanism and utilizes gear mesh locking to lock the knee during stance phase. Functionally, the modeling of the ACL and the PCL in the cross-linked spring mechanism provides similar swing assistance as hydraulic mechanisms in the Ossur Total Knee. Due to 3D printing and modeling technology, the dimensions of the anatomically scalable transfemoral prosthetic knee can be personalized and scaled to match that of the patient quickly and cost-effectively. Alterations can be easily made to accommodate patients with a wider range of control than the Ossur Total Knee. Finally, the carbon fiber-nylon composite composition of the anatomically scalable transfemoral prosthetic knee, compared to metal, is lighter and would require less metabolic cost from the user. The current invention uses a polycentric cross four-bar mechanism that is designed to mimic the anatomical movement of the human knee. This knee design can be tuned to offer a wide range of control from K0 to K4.

In certain embodiments, the current invention is a prosthetic knee joint having an upper femoral gear located at the distal end of a prosthetic femur and a lower tibial gear located at a proximal end of a prosthetic tibia. FIGS. 1, 2, and 3A-3C depict a rapid prototype model of the two interconnected gears, but do not provide accurate representations of the prosthetic femur or the prosthetic tibia. The figures simply include members extending from the top and bottom surfaces of the respective femoral and tibial gears to represent the general placement of a prosthetic femur and a prosthetic tibia. It should also be noted that the current invention is preferably used with a transfemoral amputation, so the prosthetic femur can be individually designed to properly fit the individual's specific needs.

The representative member for the prosthetic femur is located in an anterior position with respect to the center axis of the knee joint and the longitudinal axis of the cylindrical member representative of the prosthetic tibia. The location of the prosthetic femur at a slightly anterior position to the knee center aids in locking out the knee joint. In an embodiment, the location of the femur connection point can be adjusted based on an amputee's preference.

The femoral gear includes a rotational stop at a lower anterior end of the femoral gear. The rotational stop extends downward from the bottom surface of the femoral gear in a direction opposite of the extension of the prosthetic femur. In an embodiment, the rotational stop is longitudinally aligned with the prosthetic femur. The rotational stop prevents over rotation or hyperextension of the prosthetic knee joint. The upper anterior end of the tibial gear includes a flat anterior surface to abut or mate with the rotational stop when the knee joint reaches a locked-out position.

Both the femoral gear and the tibial gear are modified to aid in locking out the knee joint. The circular gears end at their anterior portions with meshable flat racks, which not only bear the load during weight bearing and but also prevent hyperextension due to the meshing. The flat racks are located at anterior locations along the gears. More specifically, the flat rack of the femoral gear is located proximate to the rotational stop, which is on the lower section of the gear when the prosthetic femur is in a vertical orientation. The flat rack of the tibial gear is located proximate to the flat anterior surface of the tibial gear, which is on the upper section of the gear when the tibia is in a vertical orientation. As noted previously, the flat anterior surface of the tibial gear abuts or mates with the rotational stop of the prosthetic femoral gear in the locked-out position.

Both the femoral and tibial gears become rounded towards the posterior location of the prosthetic knee joint. The rounded shape is representative of a circular radius. The radius of the circular gear can be scaled to fit any amputee's anatomical femoral dimension. The rounded shape is necessary to allow the gears to passively rotate with respect to each other as the user strides.

Figure 3A:
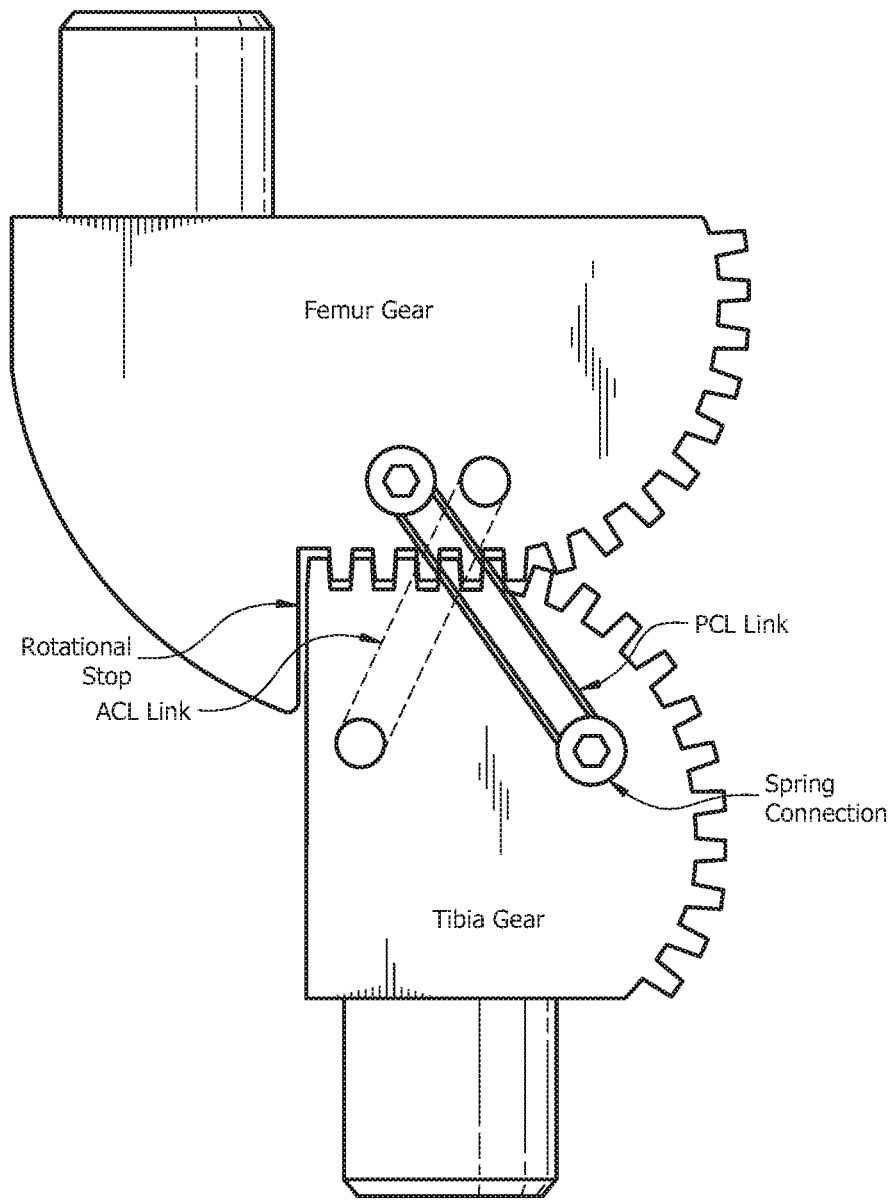
FIG. 3A is a profile view of an embodiment of the prosthetic knee joint shown as a prototype model.
Figure 3B:
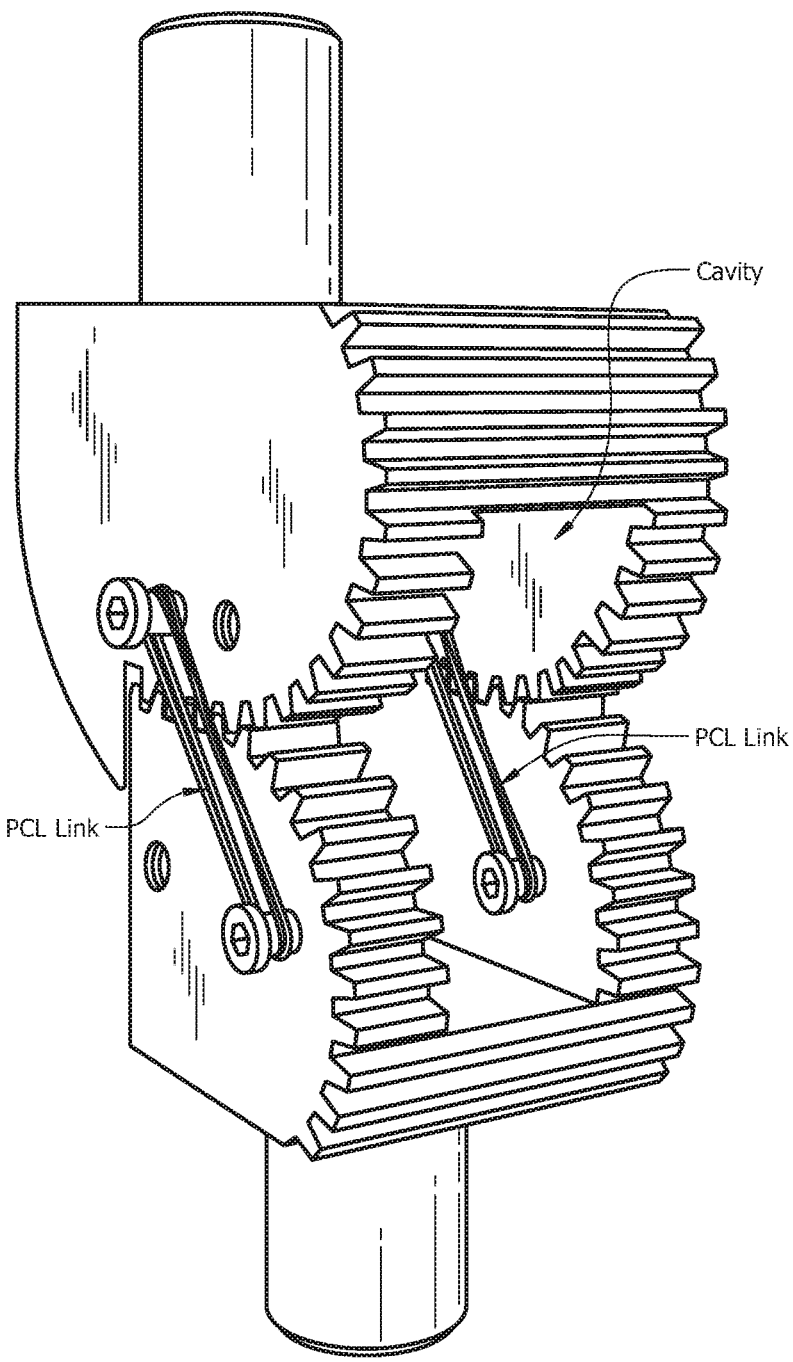
FIG. 3B is a rear perspective view of the embodiment of FIG. 3A.
Figure 3C:
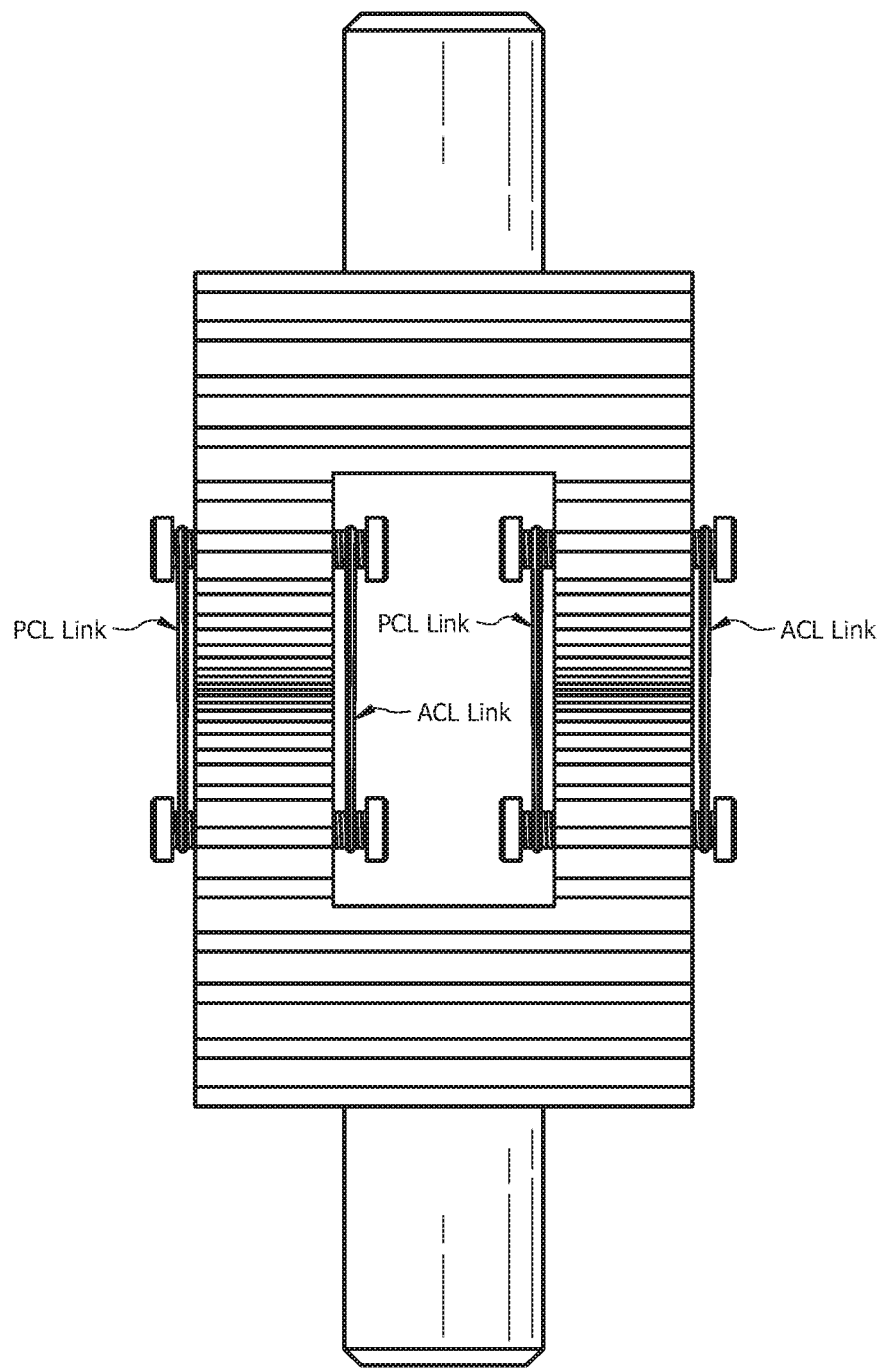
FIG. 3C is a rear view of the embodiment of FIG. 3A.

As shown in FIGS. 2 and 3A-3C, both the femoral and tibial gears have a removed interior area, such that they appear to be generally U-shaped when viewed from the front or back. In FIG. 3C the femoral gear is an inverted U-shape and the tibial gear is a righted U-shape. The removed interior area results in two parallel gears that define an interior cavity when the tibial and femoral gears are interlocked.

The current invention uses a passive locking mechanism with the same four-bar mechanism established by a natural, healthy ACL and PCL. In certain embodiments, the flexible four-bar mechanism of the current invention includes an ACL link, a PCL link, and the femoral and tibial gears on which the ACL and PCL links are connected. The flexible four-bar mechanism guides the motion of the knee and aids in the return of the knee from full flexion to extension. The flexible four-bar mechanism also couples the femoral spur gear to the tibial spur gear together and utilizes a parallel link to keep the femur and tibia from moving away from each other when the knee is active.

Still referring to FIGS. 1, 2, and 3A-3C, certain embodiments of the current invention include spring connections that can be fit with a range of springs (e.g., forming the ACL and PCL links) that vary in stiffness depending on the control level of the amputee. There are also various spring connection points or apertures disposed on the lateral surfaces of the femoral and tibial gears, allowing for different configurations of initial spring stiffness to better aid in the dynamics of the knee joint. Depending on the configuration of the springs, they can act as returning and stabilizing mechanisms. Each of the ACL and PCL links may be formed of one or more springs, but the springs should be arranged such that the ACL links/springs cross the PCL links/springs.

The prosthesis includes outer links on both of the outer lateral surfaces of the knee joint. The outer links provide lateral stability, and they support, form, and keep the knee mechanism intact. The outer links have a fixed length and are secured to the center points of the two gears. An embodiment may include variable length outer links, which may be utilized with non-circular femoral and tibial gears.

As shown in FIG. 3C, the prosthetic knee joint can be divided into two halves along a sagittal plane, such that both a left half and a right half of the knee joint include a flexible four-bar mechanism. In an embodiment, the left half includes a first PCL link located on the outer surface of the gears and a first ACL link located on the inner surface of the gears within the interior cavity. The right half includes a second ACL link located on the outer surface of the gears and a second PCL link located on the inner surface of the gears within the interior cavity. In another embodiment, the PCL link on the right half may be positioned on an outer surface of the gears, while the PCL link on the left half of the knee joint is positioned on an inner surface of the gears within the interior cavity. In turn, the ACL link on the left half can be positioned on an outer surface of the gears while the ACL link on the right half is positioned on an inner surface of the gears within the interior cavity.

In an embodiment, the ACL and PCL links are flexible spring members, having a known spring constant, attached to the gears through spring connections extending laterally outward from the surfaces of the gears in a generally perpendicular orientation with respect to the underlying surfaces. The interconnection of the PCL and ACL links with the gears through the spring connections preferably allows the ACL and PCL links to freely rotate about the spring connections. The ability to freely rotate prevents the PCL and ACL links from wrapping around the spring connections.

As highlighted in FIG. 3A, the PCL link has a tibial end connected at a posterior location on the tibial gear. The femoral end of the PCL link extends towards the center axis of the knee joint and is secured to the femoral gear at generally anterior position on the femoral gear with respect to the curved section of the femoral gear. The ACL link includes a tibial end secured at an anterior location near the flat anterior surface of the tibial gear. The ACL link extends to the femoral gear where a femoral end of the PCL link connects to the femoral gear at a posterior location on the femoral gear. The ACL link and PCL link cross each other as shown in FIG. 3A, though the PCL link is positioned here on one side of the gears and the ACL link is positioned on the opposite side of the gears (indicated by the broken lines).

Figure 4:
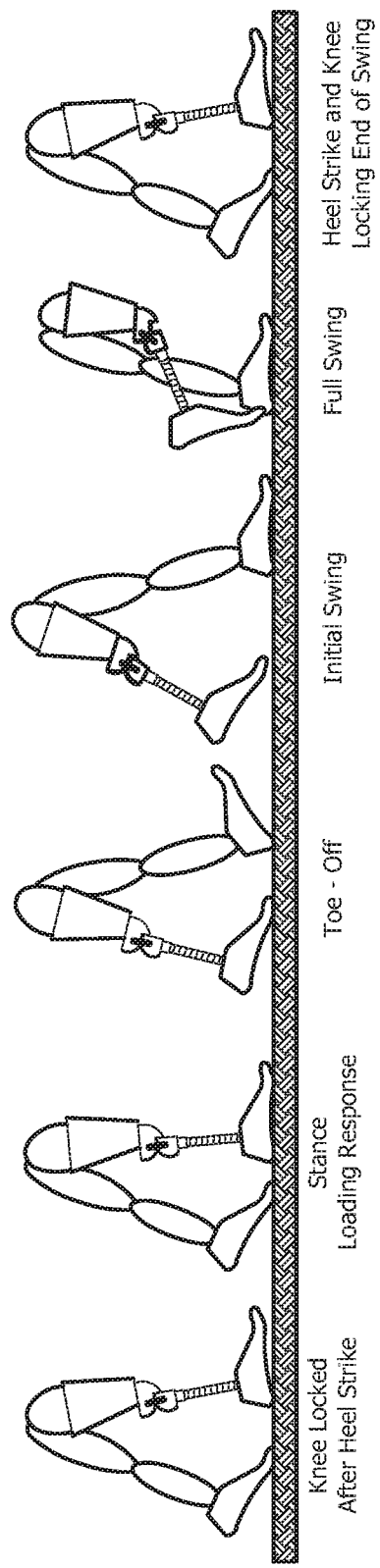
FIG. 4 depicts the action of the prosthesis during an exemplary stride.

As seen in FIG. 4, the function of the knee is relatively straightforward, and the kinematics of the mechanism mimic a natural, healthy human knee. When the user's weight is applied to the top of the femoral spur gear it locks with the tibial spur gear. The weight of the user is applied towards the anterior of the femoral spur gear in order to prevent buckling of the knee. The knee stays locked throughout the stance phase and when the user initiates swing. At toe off, the weight of the user shifts to their opposite leg and no weight is applied on the prosthetic knee. This allows the knee to flex, guided by the four-bar mechanism that mimic the ACL and PCL of a normal, healthy knee. When the user strides with the prosthesis, the flexible links are stretched to a certain length, thus increasing stiffnesses in the springs. At the terminal swing phase, just before heel strike, the flexible ACL and PCL links pull the knee joint back to the extended/locking position and the joint locks completely once the user applies weight on the prosthetic knee.

This knee prosthesis includes relatively few parts, which makes it a candidate for sustainable additive manufacturing to offer highly customized products that require minimal maintenance. The prototypes used for the experimentation discussed below, were formed of 3D printed ABS and nylon; however, it is contemplated herein that the prosthesis may be formed of aluminum, titanium, or any other material suitable for prostheses. Functional pediatric knees can be formed from these materials, and the child amputee can receive a new prosthetic knee when he/she outgrows older ones. The current prosthesis is also a viable candidate to be produced using metal additive manufacturing processes for adult sizes.

The gear design is based on several parameters disclosed in the following table.

TABLE 1

Gear design parameters for different sizes.

| Gear Parameters | Adult | Child (Assuming half the size) |
| --- | --- | --- |
| Pitch Radius (Condylar radius) | 28.5 | 14.25 |
| Teeth Pressure Angle | 14.5° | 14.5° |
| Number of Teeth in Full Gear | 25 | 25 |
| Number of Teeth in the Rack | 4 | 4 |
| Addendum | 1.14 | 0.57 |
| Diametric Pitch | 0.877 | 1.754 |
| Module | 1.14 | 0.57 |
| Velocity Ratio | 1 | 1 |

Gear Pitch

An MRI image (or other suitable imaging technique) of an intact femur of an amputee (or optionally a bilateral individual of similar proportion) is taken and used to obtain the pitch diameter of the gear used in the prosthetic knee mechanism. The pitch diameter of the gear typically is about two times (2×) the average radius of the femoral condyles, though other suitable proportions are contemplated herein as well. Radii of femoral condyles generally range from about 20-30 mm for adults [Siebold, R., et al. (2010). A computerized analysis of femoral condyle radii in ACL intact and contralateral ACL reconstructed knees using 3D CT. Knee surgery, sports traumatology, arthroscopy, 18(1), 26-31; Siu, D., et al. (1996). Femoral articular shape and geometry: a three-dimensional computerized analysis of the knee. The Journal of arthroplasty, 11(2), 166-173; Yue, B., et al. (2011). Gender differences in the knees of Chinese population. Knee surgery, sports traumatology, arthroscopy, 19(1), 80-88; Monk, A. P., et al. (2014). The shape of the distal femur. Bone Joint J, 96(12), 1623-1630].

The pitch radius used for the following experimental design was 28.5 mm, which is on the higher side of the condylar radii. The versatility and biomimetic design of the current prosthetic makes this knee unique and highly customizable. The knee also facilitates modification to add control elements that can benefit amputees with lower control since it operates using simplistic spur gears and springs. For example, a high functioning amputee may desire low stiffness for instantaneous response from the knee; alternatively, a lower functioning amputee may require higher stiffness for more control.

The tibial and femoral gears are preferably spur gears, but an embodiment may include another type of gear combination that allows the prosthetic tibia and prosthetic femur to flex in a biomimetic manner.

Study 1

The knee mechanism was tested on a single subject fitted with a prosthetic simulator. The trial was conducted on the computer assisted rehabilitation environment (CAREN) by Motek Medical. The CAREN system is equipped with a Bertec split belt treadmill, a 6 degree of freedom motion base, a ten-camera Vicon motion capture system, Bertec continuous force plates, and a panoramic screen for virtual interaction. The knee's motion was recorded using three reflective markers placed on the prosthesis to obtain the knee angles of the biomimetic knee as the subject walked on the treadmill.

Figure 5A:
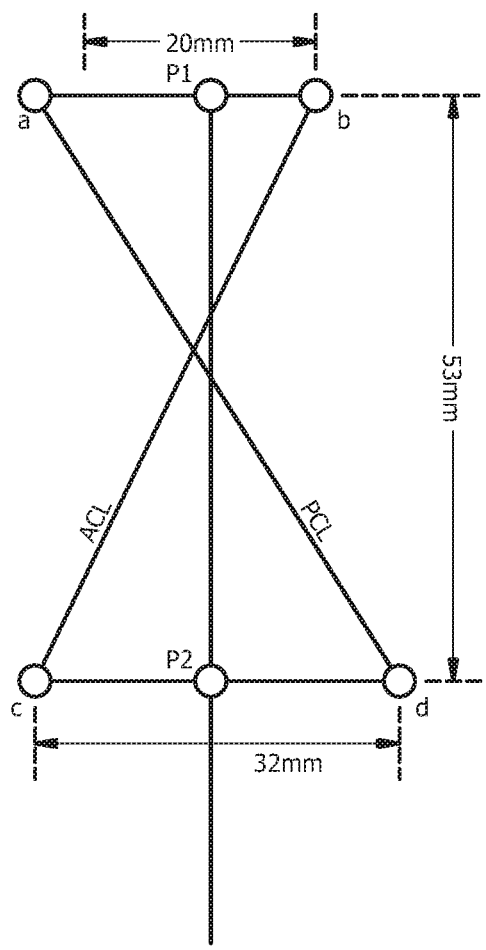
FIG. 5A is a schematic depicting a set of exemplary dimensions for the tested prototype.
Figure 5B:
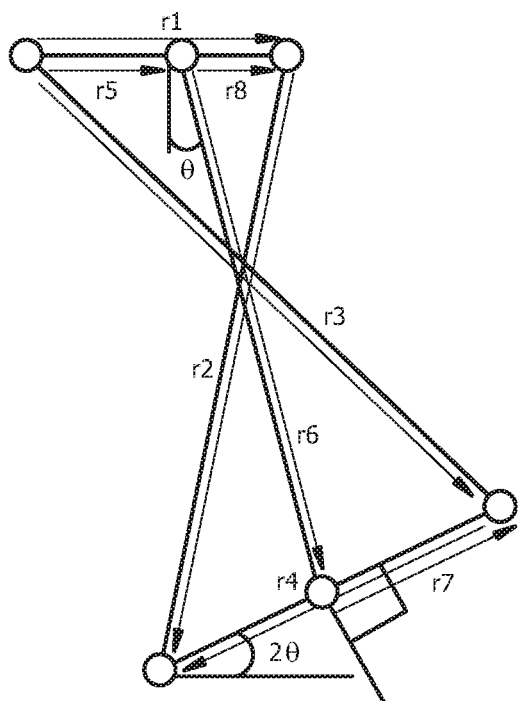
FIG. 5B depicts vector representations of the tested prototype.

The cross four-bar mechanism used for the current design, shown in FIGS. 5A-5B, is designed similarly to anatomical mechanism consisting of a healthy ACL and PCL, as seen from the sagittal plane. The mechanism presented herein has slightly different dimensions to simplify the design and make it easier to model. The mechanism includes two pivot points that can be seen as P1 and P2 in FIG. 5A. P1 is the pivoting joint for the femur, and P2 is the pivoting joint for the tibia. The link extending downwardly from the P2 joint represents the prosthetic shank. As can be seen, it is perpendicular to link c-d.

Figure 6:
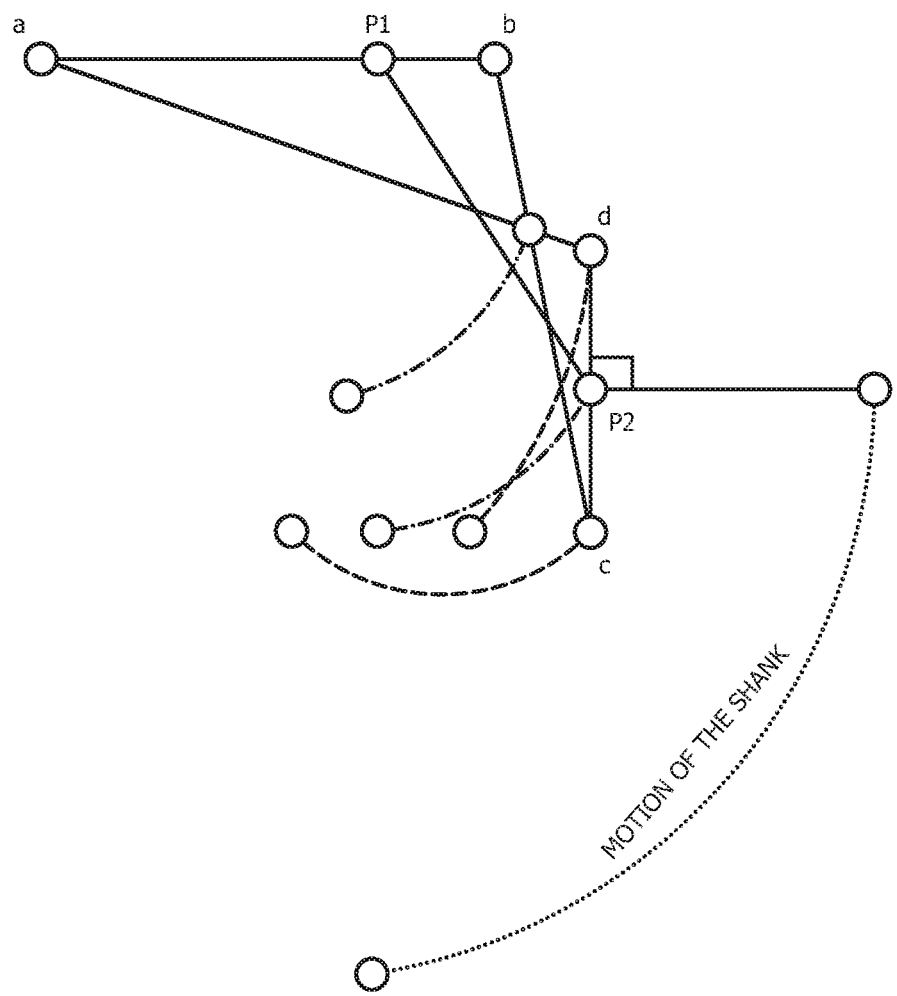
FIG. 6 depicts the motion of the mechanism with link a-b and pivot P1 fixed with the resultant motion of the shank.

Analysis of the four-bar mechanism was performed using position vector based equations. The vector representation shown in FIG. 5B includes five full vectors—one for each link—and two half vectors. The constraint applied to this mechanism is that vectors $r_1$, $r_4$, $r_5$, $r_6$, and $r_7$ are fixed, while vectors $r_3$ and $r_2$ are allowed to change in magnitude. Another major constraint is that every degree of change of theta by $r_6$ results in a change of 2*θ at $r_4$. The motion of the mechanism with the given inputs for a flexion from 0-90 degrees is shown in FIG. 6, where P1 and link a-b are fixed.

TABLE 2

Position equation parameters.

| | |
|---|---|
| $r_1 = 80$ | $\theta_1 = 0$ |
| $r_4 = 32$ | $\theta_4 = 180 + 2\theta$ |
| $r_5 = 60$ | $\theta_5 = 0$ |
| $r_8 = 20$ | $\theta_8 = 0$ |
| $r_6 = 53$ | $\theta_6 = 170 + \theta$ |
| $r_7 = 0.5 * r_4 = 16$ | $\theta_7 = 2\theta$ |

Mechanical Advantage:

$$MA = \frac{2r_a}{r_b}$$

where $r_a$=the distance from the position of rotation to the end of the foot (where tangential $V_{in}$ occurs), and $r_b$=the distance from the position of rotation to the other end of the link (where tangential $V_{out}$ occurs).

$$r_1 \cos(\theta_1) + r_2 \cos(\theta_2) = r_3 \cos(\theta_3) + r_4 \cos(\theta_4) \quad (1)$$

$$r_1 \sin(\theta_1) + r_2 \sin(\theta_2) = r_3 \sin(\theta_3) + r_4 \sin(\theta_4) \quad (2)$$

$$r_5 \cos(\theta_5) + r_6 \cos(\theta_6) + r_7 \cos(\theta_7) = r_3 \cos(\theta_3) \quad (3)$$

$$r_5 \sin(\theta_5) + r_6 \sin(\theta_6) + r_7 \sin(\theta_7) = r_3 \sin(\theta_3) \quad (4)$$

$$r_8 \cos(\theta_5) + r_2 \cos(\theta_2) + r_7 \cos(\theta_7) = r_6 \cos(\theta_6) \quad (5)$$

$$r_8 \sin(\theta_5) + r_2 \sin(\theta_2) + r_7 \sin(\theta_7) = r_6 \sin(\theta_6) \quad (6)$$

Velocity Equations:

$$\dot{r}_2 = \dot{\theta}(r_6 \sin(\theta_6 - \theta_2) - 2r_7 \sin(\theta_7 - \theta_2)) \quad (7)$$

$$\omega_2 = -\frac{\dot{\theta}}{r_2}(r_6 \cos(\theta_6 - \theta_2) + 2r_7 \cos(\theta_7 - \theta_2)) \quad (8)$$

$$\dot{r}_3 = -\dot{\theta}(r_6 \sin(\theta_6 - \theta_3) + 2r_7 \sin(\theta_7 - \theta_3)) \quad (9)$$

$$\omega_3 = \frac{\dot{\theta}}{r_3}(r_6 \cos(\theta_6 - \theta_3) + 2r_7 \cos(\theta_7 - \theta_3)) \quad (10)$$

Figure 7:
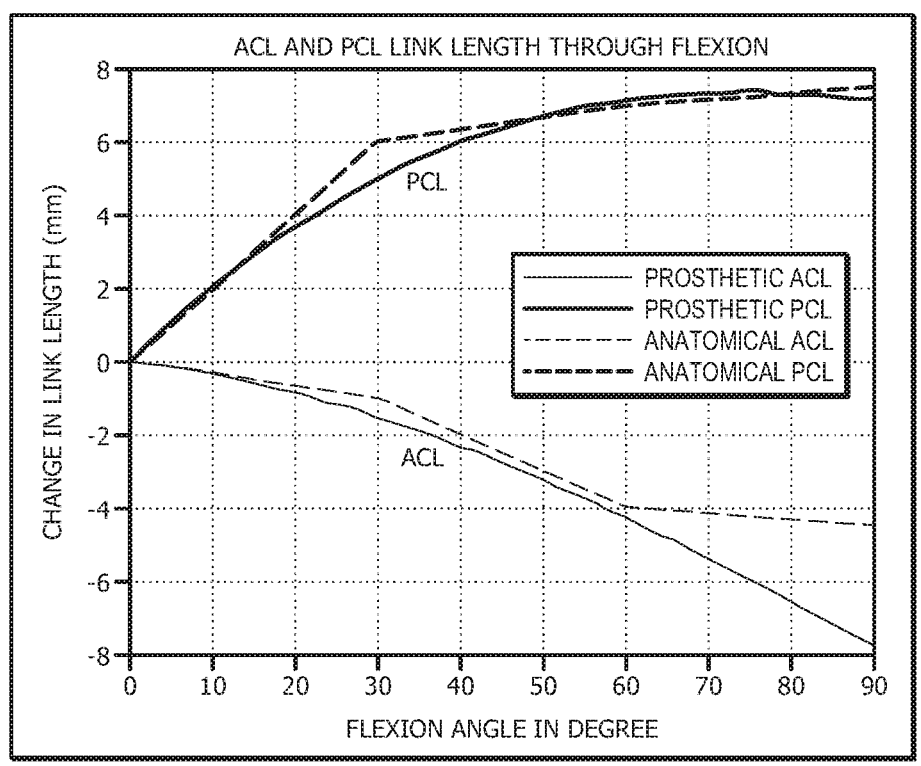
FIG. 7 is a graphical illustration depicting changes in length of the prosthetic ACL and the prosthetic PCL, as compared to anatomical data.

The equations were solved using Matlab to obtain the positions of the moving links and joints. Solving equations 1 through 4 or 3 through 6 will give the solutions for four (4) unknown variables—$r_2$, $r_3$, $\theta_2$, and $\theta_2$. When plotted, the result is motion of the system as shown in FIG. 6. The length of ACL and PCL change with the flexion angle as shown in FIG. 7. The change of link length of the prosthetic was compared to the change of length of the ACL and PCL ligament obtained from anatomical data [Li, G., et al. (2004). In vivo elongation of the anterior cruciate ligament and posterior cruciate ligament during knee flexion. The American journal of sports medicine, 32(6), 1415-1420]. It is clear from FIG. 7, specifically the similarities in link lengths through flexion and changes thereof, that the current prosthetic knee mechanism exhibits biomimetic behavior.

Figure 8:
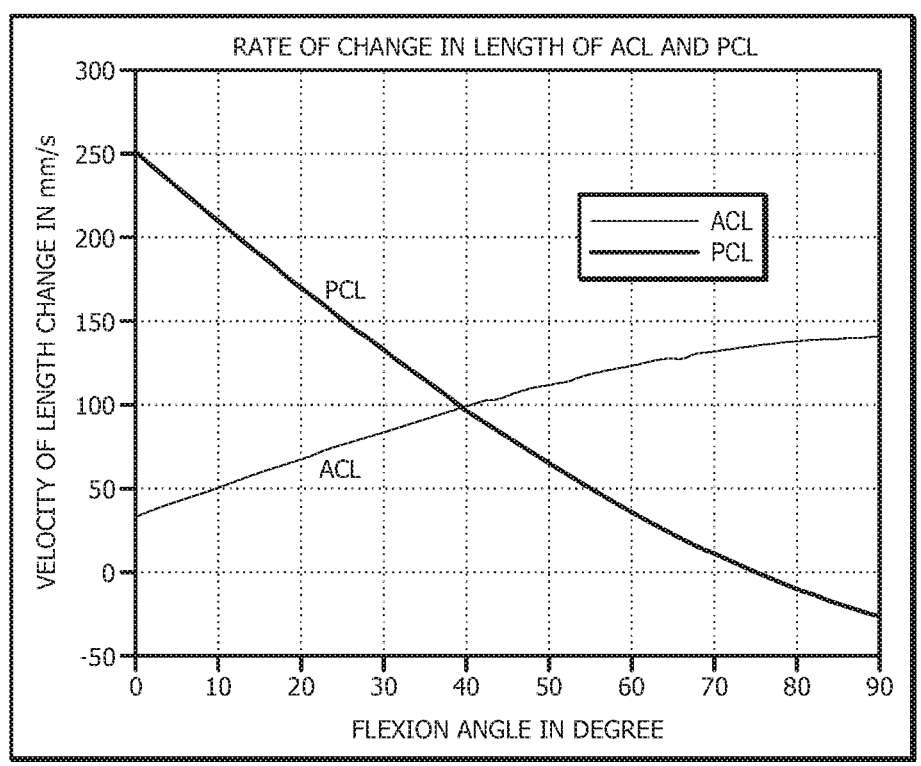
FIG. 8 is a graphical illustration depicting linear velocity profiles of the ACL and PCL as the overall flexion is moving at 10 rad/s.
Figure 9:
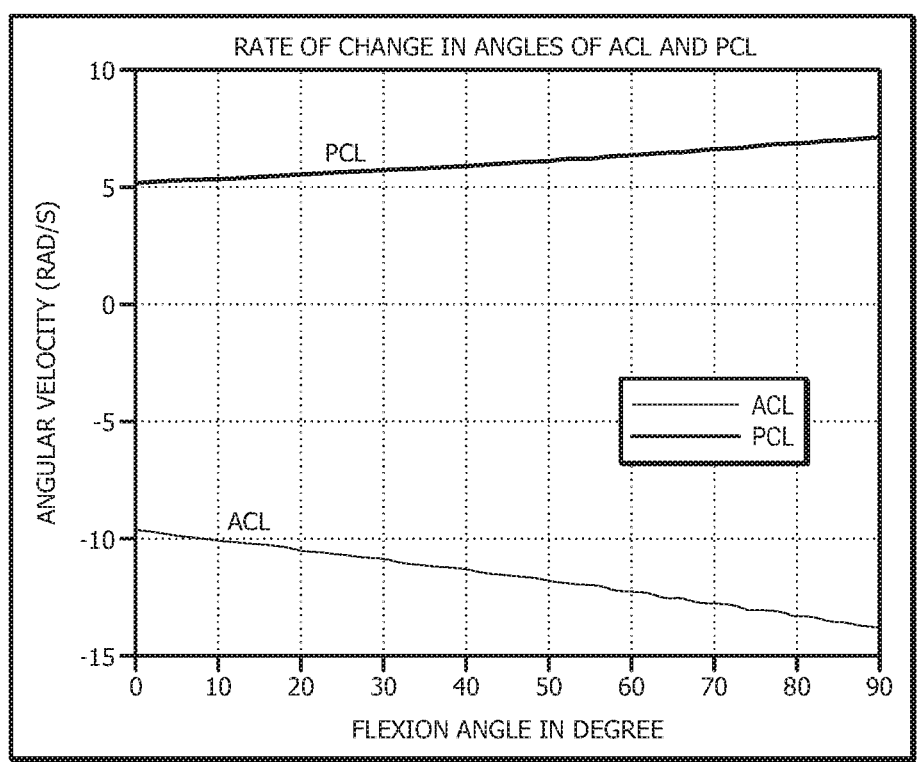
FIG. 9 is a graphical illustration depicting angular velocity profiles of the ACL and PCL as the overall flexion is moving at 10 rad/s.

The linear and angular velocity equations for change in length of ACL ($r_2$) and PCL ($r_3$) are defined in equations 7-10. The resultant linear velocities are plotted in FIG. 8, where a constant velocity of 10 rad/s was assumed, as it is reported to be the peak angular velocity during gait [McGibbon, C. A. (2012). A biomechanical model for encoding joint dynamics: applications to transfemoral prosthesis control. Journal of Applied Physiology, 112(9), 1600-1611]. The rate of change of PCL length decreases as the knee approaches full flexion. This is compensated by the ACL, which changes length at a more rapid frequency as the knee is in flexion. The angular velocity of the rate of change of the angles that ACL and PCL make with the positive x-axis also changes over flexion, as shown in FIG. 9. While there is a negative change in angular velocity for the ACL, it is a positive change for the PCL link.

Results

The results for this experiment were obtained using a 3D printed prototype. The prototype demonstrates the kinematics of the design using the minimum viable product. As previously stated, the kinematics can be tuned to better fit normal human knee motion. This can be done by adjusting the stiffness of the links or by addition of dampers to make the motion smoother.

Figure 10:
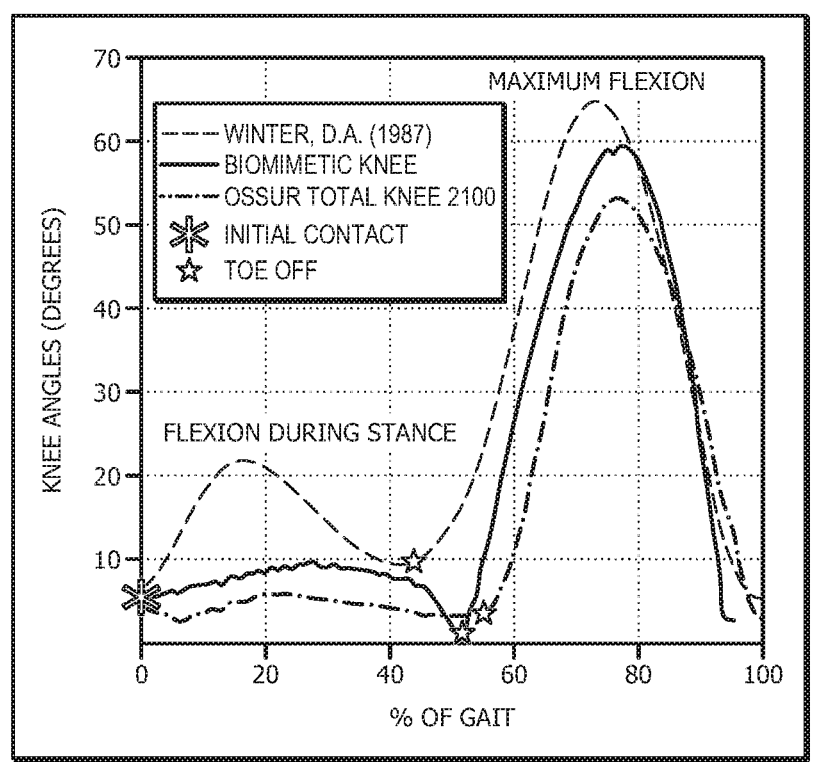
FIG. 10 is a graphical illustration depicting knee angles of (a) an embodiment of the current invention ("biomimetic knee"), (b) Ossur Total Knee 2100 [Ramakrishnan, T, et al. (2016). Combined Gait Asymmetry Metric. 38$^{th}$ Annual International Conference of the IEEE Engineering in Medicine and Biology Society (EMBC)], and (c) Winter, D. A. (1987) [Winter, D. A. (1987). The biomechanics and motor control of human gait Waterloo].

The gait data obtained was processed using a Matlab script to calculate the knee angles during gait. The results were compared to the standard knee angle data by Winter [Winter, D. A. (1987). The biomechanics and motor control of human gait Waterloo] and the prosthetic gait data was obtained with an Ossur Total Knee 2100 with hydraulic return mechanism in another study [Ramakrishnan. T, et al. (2016). Combined Gait Asymmetry Metric. 38$^{th}$ Annual International Conference of the IEEE Engineering in Medicine and Biology Society (EMBC)], as seen in FIG. 10. It is clearly shown that the current invention has more similar trends in knee angles to that of Winter's data than the Ossur Total Knee. This is because the prosthetic knee of the current invention is designed to have the same dimensions as a human knee and because the flexible four-bar mechanism helps in stabilizing the motion. However, there is a clear difference at toe-off between Winter's data and the prosthetic knee of the current invention because the prosthetic knee of the current invention is completely passive and thus generates less push-off torque. This explains the drop in knee angle just before flexion. The Ossur Total knee has a hydraulic return mechanism and hence, due to the hydraulic resistance has a smoother transition from push off to full flexion.

Figure 11:
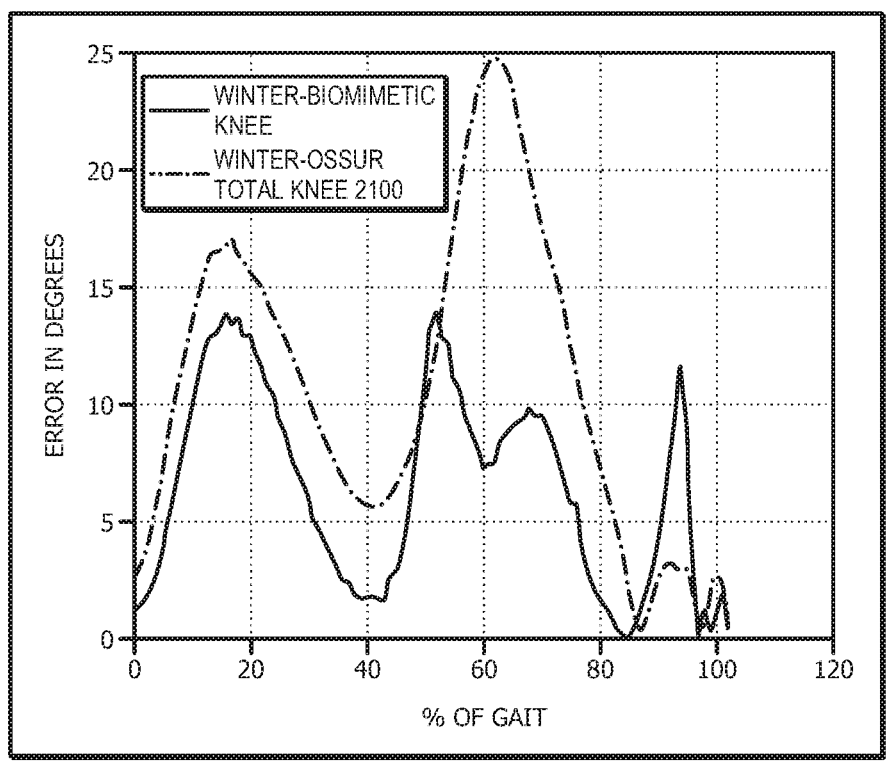
FIG. 11 is a graphical illustration depicting error between knee angles compared with the Winter Knee angle data.

The knee angles of the two prosthetic knees (current biomimetic knee and Ossur Total Knee) are compared to published gait data in FIG. 10. The error between the standard data and the two knees is shown in FIG. 11. The average error for the knee of the current invention (6.46°) is lower than the average error of the Ossur Total knee (10.7°). This is because the biomimetic knee uses a spring-based four-bar stabilization while the Ossur Total knee uses a hydraulic resistance that disrupts the natural dynamic motion of the knee by adding excess damping. This causes lower maximum flexion as seen in FIG. 10. The Ossur Total Knee also had a larger standard deviation error (6.78°) than the knee of the current invention (4.22°).

Considering the foregoing results, the prosthetic knee design of the current invention, unlike conventional prosthetic knees, can be scaled to fit any individual regardless the age, weight, height, and gender. This is because the knee is based on anatomical dimensions and scaling it will not affect the function of the mechanism. In turn, the current invention contemplates that this design can also be extended into orthotics and humanoid robotics. The addition of the flexible four-bar links can aid in the stability of these mechanisms and can assist the limb with the correct form of motion. In humanoid robotics, it could provide the necessary human like gait motions that are lacking since most robotic knees are single axis joints. An actuated version of this mechanism could offer the stability and function that is required by humanoid robots.

The knee of the current invention has the potential to behave much like an actual human knee. From the results, it is clearly better than current knee prostheses in expressing human knee kinematics [Id.]. The current knee uses a polycentric mechanism like many popular mechanisms. This offers several advantages compared to single axis or simple weight-actuated mechanisms because it helps the shank and foot clear the ground to avoid tripping. Using the current knee, the tibia gear rolls on top of the femur that helps it move in the vertical direction and also the horizontal direction, helping the foot clear the floor during terminal swing phase.

Another major advantage of this design is its flexibility to be customized. Tuning the prosthetic knee according to a person's body and gait helps in managing their quality of gait [Kark, L., et al. (2011). Patient satisfaction following lower-limb amputation: the role of gait deviation. Prosthetics and orthotics international, 35(2), 225-233]. This is beneficial to amputees in order to avoid long term injuries due to their physical asymmetry. Passive mechanisms, such as the current one, can also have simple control systems which may offer long term benefits to amputees and relieve them from expensive, loud, and inefficient active prosthetic knees.

Customization may lead this design to be used by amputees with various levels of control. This is an important factor to address with this knee design because in current prosthetic technology, there are certain types of knees that are designated for each of the K levels. This is a disparate system that can be streamlined with a highly customizable base platform that can function across the K levels. Further, the current design's ability to be scaled to any size will offer better treatment protocols and faster iterations in order to provide the best prosthetic fit for the amputee.

In conclusion, the current invention bridges an important gap in current prosthetic technology trends. The knee of the current invention can be mass produced using both traditional and modern manufacturing processes, and is also designed to reduce the cost of manufacturing, since it consists of only two major parts. This design can be used with a simple configuration of springs, along with a complex fully actuated system to control the kinematics of the knee for amputees with low muscle control.

Study 2

This study compares a transfemoral amputee's gait while using the existing Ossur Total Knee 2000 and a 3D printed anatomically scalable transfemoral prosthetic knee according to an embodiment of the current invention. The prosthetic knee according to the current invention is 3D printed out of a carbon fiber-nylon composite that has a gear-mesh coupling with a hard-stop weight-actuated locking mechanism aided by a cross-linked four-bar spring mechanism. This design can be scaled using anatomical dimensions of a human femur and tibia to have a unique fit for each user.

The transfemoral amputee who was tested is high functioning and walked on the CAREN system at a self-selected pace. The motion capture and force data that was collected showed that there were distinct differences in the gait dynamics between the current prosthetic knee and the Ossur Total Knee. The data was used to perform the Combined Gait Asymmetry Metric (CGAM), where scores revealed that the overall asymmetry of the gait on the Ossur Total Knee was more asymmetric than the current prosthetic knee. The current prosthetic knee had higher peak knee flexion that caused a large step time asymmetry. This made walking on the current prosthetic knee more strenuous due to the compensatory movements in adapting to the different dynamics. However, this issue can be overcome by tuning the cross-linked spring mechanism to better emulate the dynamics of the subject. The subject stated that the knee would be good for daily use and has the potential to be adapted as a running knee.

Design

Figure 12A:
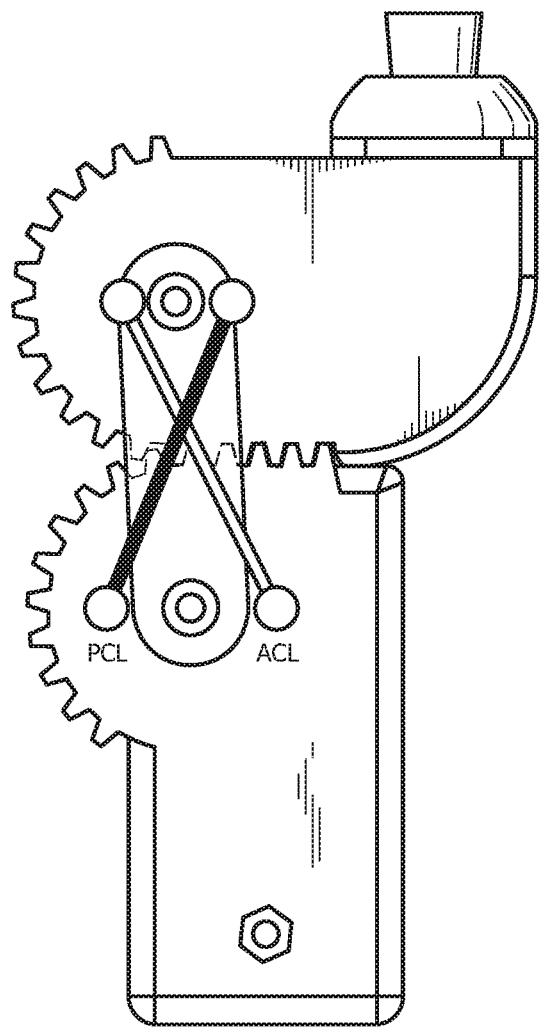
FIG. 12A depicts spring configuration as used in the example/study discussed herein.
Figure 12B:
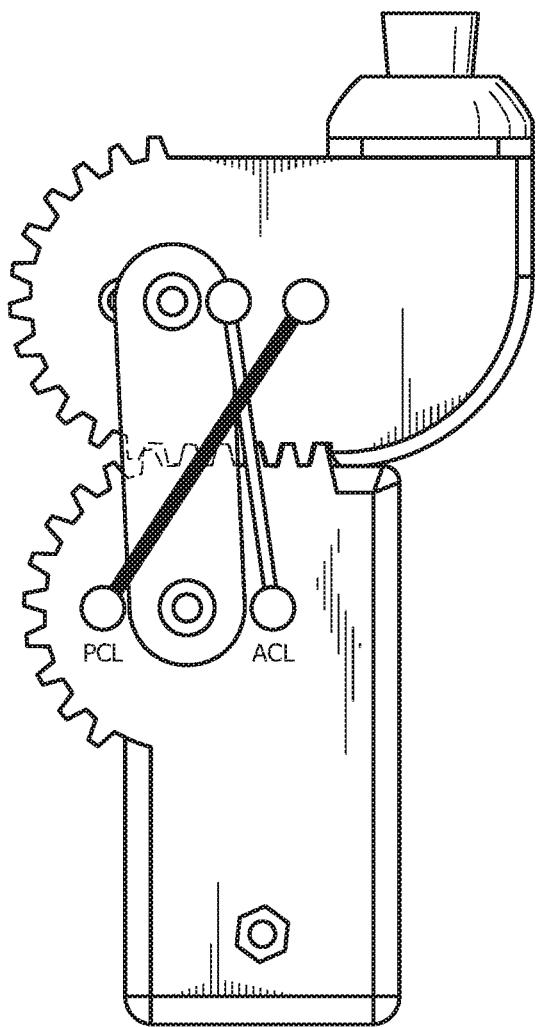
FIG. 12B depicts spring configuration for faster extension.
Figure 13:
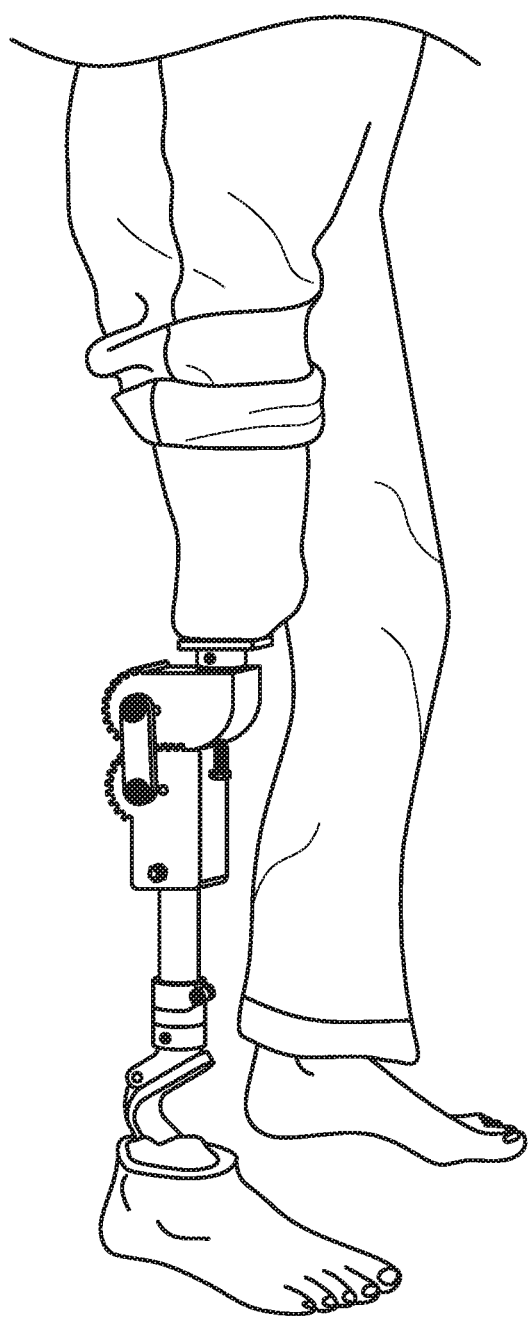
FIG. 13 depicts an amputee wearing a knee prosthesis, according to an embodiment of the current invention.

The prosthetic knee used in this study has two parts formed of a carbon fiber-nylon composite. The prosthetic knee includes a gear mesh locking mechanism that is aided by a cross-linked spring mechanism that functions similar to the ACL and PCL of the human body (see FIGS. 12A-12B). The springs used for this study were metallic. A preliminary prototype of this prosthetic knee was used to obtain the mechanism's kinematics [T. Ramakrishnan, et al., "Biomimetic transfemoral knee with gear mesh locking mechanism," International Journal of Engineering Research & Innovation, 2017], as discussed in Study 1. The femoral gear attaches to the socket, and the tibial gear holds the foot and pylon assembly, as shown in FIG. 13. The femoral and tibial gears are designed based on condylar radius of an adult human, which ranges from 18-30 mm [R. Siebold, et al., "A computerized analysis of femoral condyle radii in acl intact and contralateral acl reconstructed knees using 3d ct," Knee surgery, sports traumatology, arthroscopy, vol. 18, no. 1, pp. 26-31, 2010; D. Siu, et al., "Femoral articular shape and geometry: a three-dimensional computerized analysis of the knee," The Journal of arthroplasty, vol. 11, no. 2, pp. 166-173, 1996; B. Yue, et al., "Gender differences in the knees of Chinese population," Knee surgery, sports traumatology, arthroscopy, vol. 19, no. 1, pp. 80-88, 2011]. The full gears are designed to have about 25 teeth at an approximately 14.5° pressure angle. The gears are held together by an exterior link that is laser-cut out of Delrin, a strong acrylic plastic material. The femoral gear attaches to the socket by means of a conventional titanium pyramid head or other suitable connecting mechanism. The pylon and foot assembly is connected to the tibia gear by means of a precision fit with a bolt connector. A comparison of the specifications of the two knees is shown in Table 3.

TABLE 3

Prosthetic knee specifications.

| Parameters | Ossur Total Knee 2000 | Current Biomimetic Knee |
|---|---|---|
| Amputation Level | Transfemoral | Transfemoral |
| Impact Level | K2-K4 | K2-K4 |
| Max. Patent Weight | 100 kg | 110 kg |
| Knee Weight | 690 g | 701.5 g |
| Build Height | 173 mm | 185 mm |
| Flexion | 160° | 180° |

The mechanism of the Ossur Total Knee and the mechanism of the prosthetic knee mechanisms are quite different. The Ossur Total Knee has a five-bar mechanism that is aided by a hydraulic return mechanism. The current prosthetic knee uses the curvature of the femoral and tibial gears to lock and unlock, while the cross-linked spring mechanism acts as a return mechanism. This can be seen in FIG. 12A. At heel strike, the femoral and tibial gears have a hard-stop at full extension, after which the loading of the user's weight keeps it locked through stance phase. The gears also function in locking, as they do not allow the femur and tibia to slide during stance loading. This results in the gear mesh coupled with a hard-stop and a weight-actuated locking mechanism of the prosthetic knee, as contrasted to the geometric and hard-stop locking mechanism of the Ossur Total Knee. The ability to customize prosthetics is of growing interest in the field of prosthetics, as more users prefer components that are made according to their individual preferences. For example, the amputee subject from the current study here reported that the ability of the current transfemoral prosthetic knee to flex more than the Ossur Total Knee allowed her to kneel more comfortably.

Methods

The subject for this study is a 37-year-old female, high-functioning, transfemoral amputee. The experiments were conducted on the CAREN system. The CAREN system is equipped to provide continuous motion capture and force plate data collection. The subject walked on the treadmill, at a velocity that is obtained from a standard 10-meter walk test; in this case, it was 1.4 m/s. Eighteen (18) reflective markers were used for motion capture; specifically, the markers were positioned to facilitate capturing primary joint, hip, knee, and ankle motions. The motion capture and kinetic data obtained was processed using a Matlab script that assessed eleven (11) different spatio-temporal, kinematic, and kinetic gait parameters. The Combined Gait Asymmetry Metric [T. Ramakrishnan, et al., "Combined gait asymmetry metric," in 38th Annual International Conference of the IEEE Engineering in Medicine and Biology Society (EMBC), 2016] was also used to measure the overall asymmetry of the two gait patterns.

Results

Figure 14:
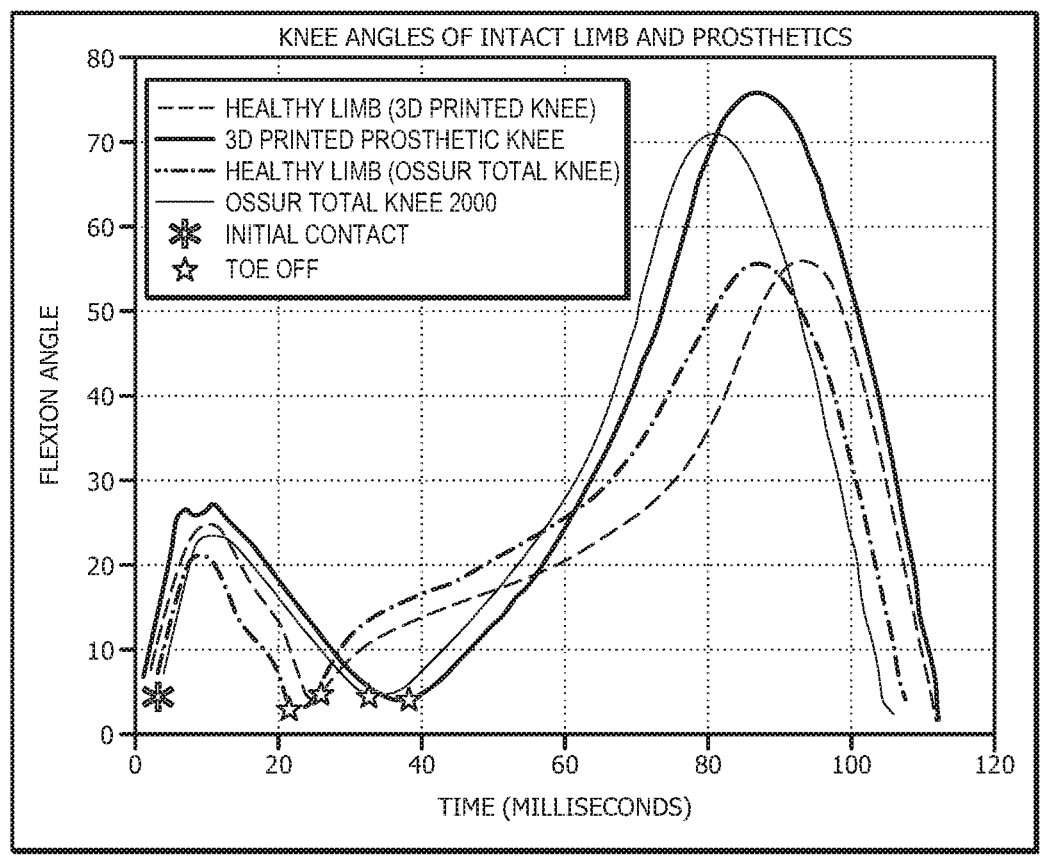
FIG. 14 is a graphical illustration comparing knee angles of a healthy limb (3D printed knee), a 3D printed prosthetic knee according to an embodiment of the current invention, a healthy limb (based on Ossur Total Knee), and Ossur Total Knee 2000.

The apparent difference between the prosthetic knees can be evaluated using the knee angles shown in FIG. 14. It can be seen that the step time on both the right and left sides take longer on the current knee, as compared to the Ossur Total Knee. This may be because the amputee uses the Ossur Total Knee every day and is aware of the knee's nuances that help her achieve shorter step times. The amputee also reported that she felt the current knee was lighter and that she had to wait for the terminal impact of the knee before she could shift her weight over to the prosthetic. This can be optimized by changing the cross-linked spring linkage inside the knee to help return the shank faster, thereby improving cadence by decreasing step times. Another feature that is clearly seen from the knee angles is the magnitude of maximum flexion. The current knee has higher peak flexion compared to the Ossur Total Knee due to the lower resistance offered by the internal mechanism of the current knee. This is another cause for longer flexion times that can be mitigated by changing the configurations of the return mechanism (see FIG. 12B).

Figure 15A:
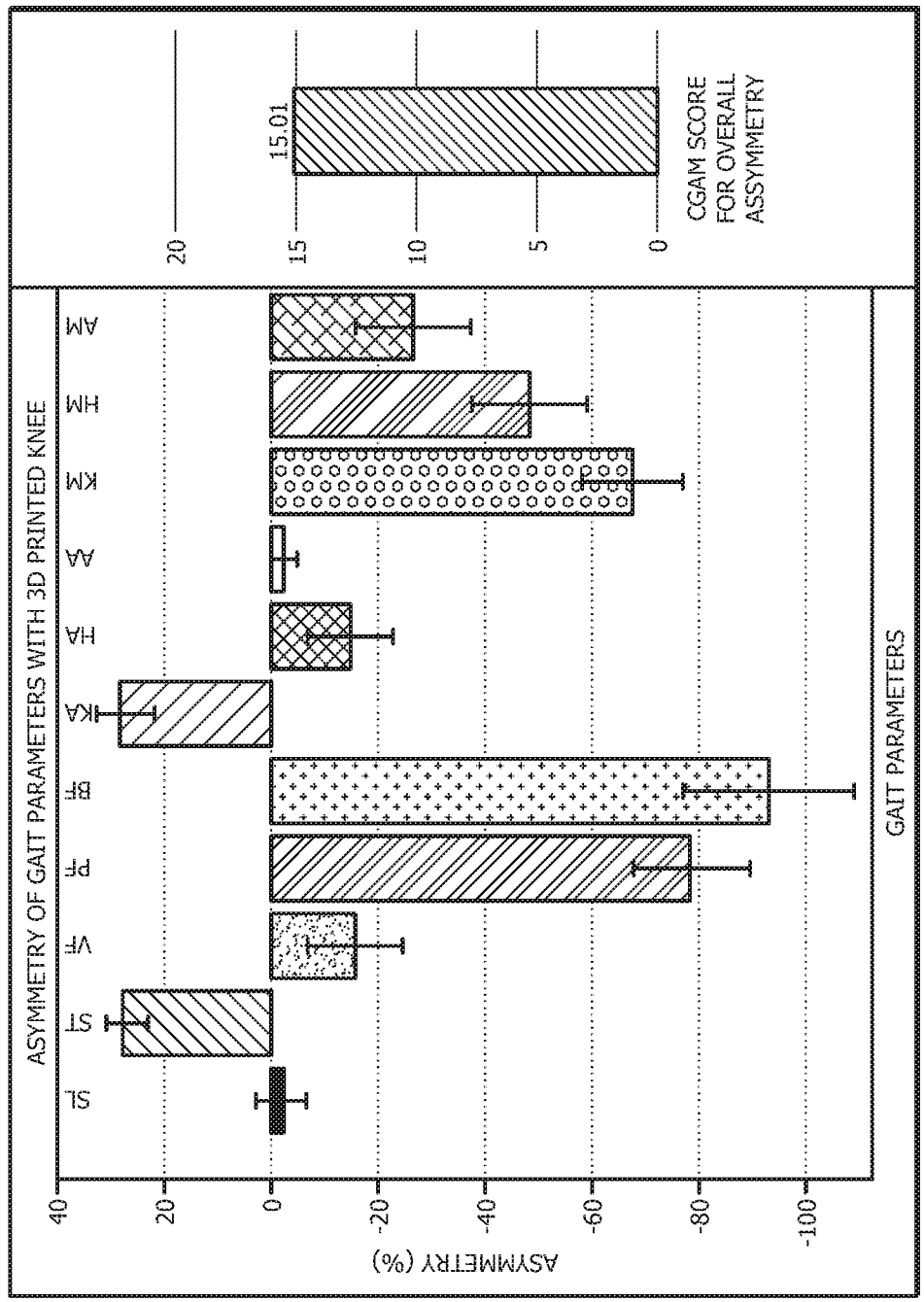
FIG. 15A depicts Combined Gait Asymmetry Metric (CGAM) scores for a knee prosthesis, according to an embodiment of the current invention [Legend: SL—Step Length, ST—Step Time, VF—Vertical Force, PF—Push Off Force, BF—Braking Force, KA—Knee Angle, HA—Hip Angle, AA—Ankle Angle, KM—Knee Moment, HM—Hip Moment, AM—Ankle Moment].
Figure 15B:
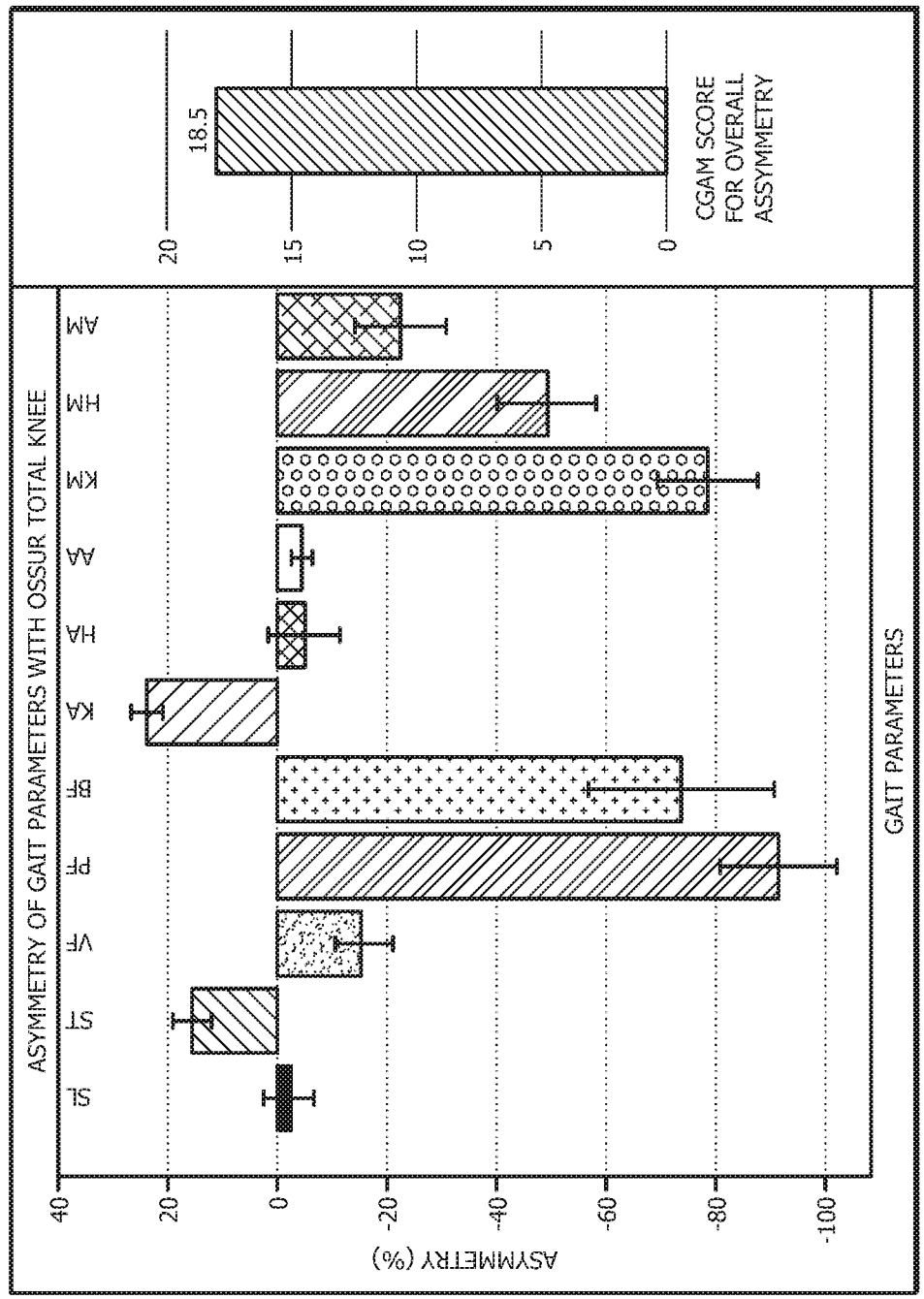
FIG. 15B depicts CGAM scores for the Ossur Total Knee [Legend: SL—Step Length, ST—Step Time, VF—Vertical Force, PF—Push Off Force, BF—Braking Force, KA—Knee Angle, HA—Hip Angle, AA—Ankle Angle, KM—Knee Moment, HM—Hip Moment, AM—Ankle Moment].

CGAM scores were calculated [Id.] to obtain a sense of the overall asymmetry of these two different gait patterns. CGAM scores were calculated using a modified Mahalanobis distance [P. C. Mahalanobis, "On the generalized distance in statistics," Proceedings of the National Institute of Sciences (Calcutta), vol. 2, pp. 49-55, 1936] that finds the distances using all eleven gait asymmetry parameters. The distances are weighed according to the inverse covariance among the eleven gait parameters, as can be seen in FIGS. 15A-15B. This form of combining the asymmetries of different gait parameters gives rise to the CGAM scores that represent the overall asymmetry. The asymmetry observed in knee angles can also be seen in FIGS. 15A-15B, where the average peak knee angle asymmetry of the current knee is larger than the average peak knee angle asymmetry of the Ossur Total Knee. This resulted in a larger step time and in braking force asymmetry. The magnitude of the CGAM score indicates the degree of overall asymmetry in the person's gait. In this case, the subject's gait with the Ossur Total Knee is more asymmetric than the current biomimetic knee.

In light of the foregoing results, it can be seen that the current 3D printed anatomically scalable transfemoral prosthetic knee is a simple mechanism that has the potential to be customized on a subjective basis, based on needs of the end-user. 3D printing prosthetic knees will help reduce the cost of manufacturing while allowing users to choose desired features from the mechanism. This would also permit scaling of the same design over different anatomical sizes from children to adults and also modifying them for male and female users. This flexibility is not seen with traditional designs that can only be made at certain sizes and shapes due to the limitations of conventional manufacturing processes.

The results of the current study show specific differences between the change in gait dynamics between the current knee and the Ossur Total Knee. The gait with the Ossur Total Knee has lower peak joint flexion, symmetric step time, and braking forces. However, gait with the Ossur Total Knee resulted in an overall more asymmetric gait in the CGAM score compared to the gait with the current knee. This asymmetry may be a result of the subject being more willing to shift her weight onto the Ossur Total Knee because the subject uses it every day. It is also possible that the subject's compensation to the current knee's dynamics, such as the higher peak knee flexion, resulted in a more symmetric gait. The current knee can be customized by adjusting the cross-linked spring mechanism inside the knee to a configuration shown in FIG. 12B from FIG. 12A. Using an ACL link/spring with greater stiffness will restrict the peak knee flexion and reduce the total time of knee flexion. Improving overall symmetry of prosthetic gait can bring about more comfortable and stable gait that does not cause long term damage to the residual limb and the musculoskeletal system due to the compensation. The current prosthetic knee utilizes a simplistic design to help the amputee to walk with a lower CGAM score, which can provide long-term benefits for the amputee. The subject herein was comfortable with the current knee from the first fitting. It was observed that the low resistance provided by the mechanism was better for ambulatory walking and that the knee can potentially be used for running in future iterations.

In conclusion, comparing the novel 3D printed anatomically scalable transfemoral prosthetic knee to a tried and tested Ossur Total Knee has shown that there is potential for specialized 3D printed knee designs. The simple design of the scalable transfemoral prosthetic knee allowed for the amputee to quickly adjust to its dynamics. The amputee also gave positive feedback regarding the level of use of the anatomically scalable transfemoral prosthetic knee design. Future studies will look at more optimized version that are less straining for the user yet still showcase the overall symmetric gait of the anatomically scalable transfemoral prosthetic knee. This can be accomplished by using a new combination of materials to make the designs lighter and stronger. The existing design could also be modified through changing the configuration of the cross-linked springs to better emulate swing times of the subject.

Glossary of Claim Terms

About: This term is used herein to refer to approximately or nearly and in the context of a numerical value or range set forth means±15% of the numerical. In an embodiment, the term "about" can include traditional rounding according to significant figures of the numerical value. In addition, the phrase "about 'x' to 'y'" includes "about 'x' to about 'y'".

Biomimetic: This term is used herein to refer to a prosthetic that is modeled after a living or healthy limb, primarily from a functional standpoint, such that particular structures of the prosthetic are configured to act like corresponding structures of the healthy limb.

Ligament link: This term is used herein to refer to an elastic or biased element that directly or indirectly couples two structures (e.g., gears) together and facilitates the rotation of the structures relative to each other.

Meshable relationship: This term is used herein to refer to an association between two gears, where the two components mesh together via their teeth.

Passive: This term is used herein to refer to an apparatus, or component thereof, that does not require power or other actuation in order to function.

Prosthetic: This term is used herein to refer to a structural component being artificial and acting as a substitute for a user's body part (specifically a leg or portion thereof here).

Residual or impaired limb connector: This term is used herein to refer to an individual's appendage that is compromised, amputated, or otherwise in need of an aid for full functioning.

Shank: This term is used herein to refer to the portion of a leg or prosthetic between the knee and the ankle/foot.

Substantially overlying relation: This term is used herein to refer to one structural component being positioned above another structural component, either directly above or slightly offset. For example, the point of connection of the prosthetic femur can be slightly anterior to the knee center to aid in the locking of the knee mechanism. This connection point may also be adjusted based on amputee preference. Having an anterior connection gives the amputee more control.

Substantially semi-circular: This term is used herein to refer to a shape of a structure, such as a gear, having a semi-circular appearance. An example can be seen in FIGS. 3A-3C, where the gears have a semi-circular appearance but are not exactly semi-circular.

Upright position: This term is used herein to refer to a configuration of the prosthesis in a substantially linear position, akin to an individual standing straight up to where the femur and tibia form a substantially straight line.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A biomimetic, prosthetic knee apparatus, comprising:
   a femoral gear having a curved posterior side with an array of femoral teeth disposed along a bottom side and the curved posterior side of the femoral gear;
   a tibial gear having a curved posterior side with an array of tibial teeth disposed along a top side and the curved posterior side of the tibial gear,
   wherein the femoral gear is disposed in substantially overlying relation to the tibial gear in an upright position,
   wherein the femoral teeth and the tibial teeth engage in a meshable relationship with each other,
   wherein the curved posterior side of the femoral gear and the curved posterior side of the tibial gear are aligned with one another, such that the femoral gear and the tibial gear are posteriorly rotatable relative to each other along curved posterior side of the femoral gear and the curved posterior side of the tibial gear, with the femoral teeth and the tibial teeth meshing with each other as the femoral gear and tibial gear rotate relative to each other;
   an anterior hard-stop that prevents anterior rotation of the femoral gear or the tibial gear when the femoral gear and the tibial gear are in the upright position; and
   one or more ligament links having a first end secured on the femoral gear and a second end secured to the tibial gear, wherein the one or more ligament links has a biased force that facilitates flexion-extension of the femoral gear and the tibial gear relative to each other, the one or more ligament links including:
      an ACL link secured to the femoral gear in a posterior position and secured to the tibial gear in an anterior position, such that the ACL link extends in a posterior-to-anterior direction in the upright position of the femoral and tibial gears, and
      a PCL link secured to the femoral gear in an anterior position and secured to the tibial gear in a posterior position, such that the PCL link extends in an anterior-to-posterior direction in the upright position of the femoral and tibial gears.

2. A biomimetic, prosthetic knee apparatus as in claim 1, wherein
   a top side of the femoral gear is coupled to a bottom side of a prosthetic femur, such that the femoral gear and the prosthetic femur rotate together,
   a bottom side of the tibial gear is coupled to a top side of a prosthetic tibia, such that the tibial gear and the prosthetic tibia rotate together, and
   the prosthetic knee apparatus is disposed between the prosthetic femur and the prosthetic tibia.

3. A biomimetic, prosthetic knee apparatus as in claim 1, wherein each gear of the femoral gear and the tibial gear is substantially semi-circular in shape with linear portions that mesh with each other in the upright position and curved portions that mesh with each other during rotation.

4. A biomimetic, prosthetic knee apparatus as in claim 1, wherein the anterior hard-stop includes:
   an anterior femoral stop extending downwardly along the femoral gear; and
   an anterior tibial stop extending upwardly along the tibial gear, wherein the femoral stop prevents anterior rotation of the tibial gear when the femoral stop and the tibial stop abut each other, wherein the femoral stop and the tibial stop abut each other in the upright position.

5. A biomimetic, prosthetic knee apparatus as in claim 1, wherein
the femoral gear includes two sets of teeth positioned on lateral sides of the knee apparatus,
the tibial gear includes two sets of teeth positioned on the lateral sides of the knee apparatus, and
corresponding femoral and tibial teeth on the lateral sides of the knee apparatus mesh with each other, defining an open space therebetween.

6. A biomimetic, prosthetic knee apparatus as in claim 5, wherein the ACL link is a first ACL link and the PCL link is a first PCL link, further comprising:
a second ACL link secured to the femoral gear in a posterior position and secured to the tibial gear in an anterior position, such that the second ACL link extends in a posterior-to-anterior direction in the upright position of the femoral and tibial gears, wherein the second ACL link is disposed on a lateral inner surface of a second set of corresponding teeth of the femoral and tibial gears, and
a second PCL link secured to the femoral gear in an anterior position and secured to the tibial gear in a posterior position, such that the second PCL link extends in an anterior-to-posterior direction in the upright position of the femoral and tibial gears, wherein the second PCL link is disposed on a lateral inner surface of the first set of corresponding teeth of the femoral and tibial gears.

7. A biomimetic, prosthetic knee apparatus as in claim 1, wherein the one or more ligament links includes at least two ligament links, wherein the at least two ligament links operate via a cross-linked four-bar spring mechanism that mimics an ACL and a PCL of a healthy knee.

8. A biomimetic, prosthetic knee apparatus as in claim 1, wherein the femoral teeth of the femoral gear and the tibial teeth of the tibial gear have a pressure angle of about 14.5°.

9. A passive transfemoral prosthesis, comprising:
a prosthetic femur having a top side and a bottom side, wherein the top side of said prosthetic femur is configured to be coupled to a residual or impaired limb connector in underlying relation to the residual or impaired limb connector;
a prosthetic shank having a top side and a bottom side, wherein the prosthetic shank is rotatable relative to the prosthetic femur, wherein the prosthetic shank is passive;
a prosthetic foot assembly disposed in underlying relation to the prosthetic shank; and
a biomimetic, prosthetic knee apparatus coupled to and disposed between the prosthetic femur and the prosthetic shank, wherein the prosthetic knee apparatus comprises:
a femoral gear having a curved posterior side with an array of femoral teeth disposed along a bottom side and the curved posterior side of the femoral gear,
a tibial gear having a curved posterior side with an array of tibial teeth disposed along a top side and the curved posterior side of the tibial gear,
wherein the femoral gear is disposed in substantially overlying relation to the tibial gear in an upright position,
wherein the femoral teeth and the tibial teeth engage in a meshable relationship with each other,
wherein the curved posterior side of the femoral gear and the curved posterior side of the tibial gear are aligned with one another, such that the femoral gear and the tibial gear are posteriorly rotatable relative to each other along the curved posterior side of the femoral gear and the curved posterior side of the tibial gear with the femoral teeth and the tibial teeth meshing with each other as the femoral gear and tibial gear rotate relative to each other,
an anterior hard-stop that prevents anterior rotation of the femoral gear or the tibial gear when the femoral gear and the tibial gear are in the upright position, and
one or more ligament links having a first end secured on the femoral gear and a second end secured to the tibial gear, wherein the one or more ligament links has a biased force that facilitates flexion-extension of the femoral gear and the tibial gear relative to each other,
wherein each gear of the femoral gear and the tibial gear is substantiality semi-circular in shape with linear portions that mesh with each other in the upright position and curved portions that mesh with each other during rotation.

10. A passive transfemoral prosthesis as in claim 9, wherein the anterior hard-stop includes:
an anterior femoral stop extending downwardly along the femoral gear; and
an anterior tibial stop extending upwardly along the tibial gear, wherein the femoral stop prevents anterior rotation of the tibial gear when the femoral stop and the tibial stop abut each other, wherein the femoral stop and the tibial stop abut each other in the upright position.

11. A passive transfemoral prosthesis as in claim 9, wherein the one or more ligament links includes:
an ACL link secured to the femoral gear in a posterior position and secured to the tibial gear in an anterior position, such that the ACL link extends in a posterior-to-anterior direction in the upright position of the femoral and tibial gears, and
a PCL link secured to the femoral gear in an anterior position and secured to the tibial gear in a posterior position, such that the PCL link extends in an anterior-to-posterior direction in the upright position of the femoral and tibial gears.

12. A passive transfemoral prosthesis as in claim 9, wherein
the femoral gear includes two sets of teeth positioned on lateral sides of the knee apparatus,
the tibial gear includes two sets of teeth positioned on the lateral sides of the knee apparatus, and
corresponding femoral and tibial teeth on the lateral sides of the knee apparatus mesh with each other, defining an open space therebetween.

13. A passive transfemoral prosthesis as in claim 12, wherein the one or more ligament links includes:
a first ACL link secured to the femoral gear in a posterior position and secured to the tibial gear in an anterior position, such that the first ACL link extends in a posterior-to-anterior direction in the upright position of the femoral and tibial gears, wherein the first ACL link is disposed on a lateral outer surface of a first set of corresponding teeth of the femoral and tibial gears,
a second ACL link secured to the femoral gear in a posterior position and secured to the tibial gear in an anterior position, such that the second ACL link extends in a posterior-to-anterior direction in the upright position of the femoral and tibial gears, wherein the second ACL link is disposed on a lateral inner surface of a second set of corresponding teeth of the femoral and tibial gears, a first PCL link secured to the femoral gear in an anterior position and secured to the tibial gear in a posterior position, such that the first PCL link extends in an anterior-to-posterior direction in the upright position of the femoral and tibial gears, wherein the first PCL link is disposed on a lateral outer surface of the second set of corresponding teeth of the femoral and tibial gears, and a second PCL link secured to the femoral gear in an anterior position and secured to the tibial gear in a posterior position, such that the second PCL link extends in an anterior-to-posterior direction in the upright position of the femoral and tibial gears, wherein the second PCL link is disposed on a lateral inner surface of the first set of corresponding teeth of the femoral and tibial gears.

14. A passive transfemoral prosthesis as in claim 9, wherein the one or more ligament links includes at least two ligament links, wherein the at least two ligament links operate via a cross-linked four-bar spring mechanism that mimics an ACL and a PCL of a healthy knee.

15. A passive transfemoral prosthesis as in claim 9, wherein the prosthetic femur is configured to be coupled to the residual or impaired limb connector via a titanium pyramid head, and the prosthetic shank is coupled to the prosthetic foot assembly via a bolt connector.

16. A passive transfemoral prosthesis as in claim 9, wherein the femoral teeth of the femoral gear and the tibial teeth of the tibial gear have a pressure angle of about 14.5°.

17. A passive transfemoral prosthesis, comprising:
a prosthetic femur having a top side and a bottom side, wherein the top side of said prosthetic femur is configured to be coupled to a residual or impaired limb connector in underlying relation to the residual or impaired limb connector, wherein the prosthetic femur is configured to be coupled to the residual or impaired limb connector via a titanium pyramid head;
a prosthetic shank having a top side and a bottom side, wherein the prosthetic shank is rotatable relative to the prosthetic femur, wherein the prosthetic shank is passive, wherein the prosthetic shank is coupled to the prosthetic foot assembly via a bolt connector;
a prosthetic foot assembly disposed in underlying relation to the prosthetic shank; and
a biomimetic, prosthetic knee apparatus coupled to and disposed between the prosthetic femur and the prosthetic shank, wherein the prosthetic knee apparatus comprises:
a femoral gear having a curved posterior side with an array of femoral teeth disposed along a bottom side and the curved posterior side of the femoral gear;
a tibial gear having a curved posterior side with an array of tibial teeth disposed along a top side and the curved posterior side of the tibial gear,
wherein the femoral gear is disposed in substantially overlying relation to the tibial gear in an upright position,
wherein the femoral teeth and the tibial teeth engage in a meshable relationship with each other, wherein the femoral teeth of the femoral gear and the tibial teeth of the tibial gear have a pressure angle of about 14.5°,
wherein the curved posterior side of the femoral gear and the curved posterior side of the tibial gear are aligned with one another, such that the femoral gear and the tibial gear are posteriorly rotatable relative to each other along the curved posterior side of the femoral gear and the curved posterior side of the tibial gear with the femoral teeth and the tibial teeth meshing with each other as the femoral gear and tibial gear rotate relative to each other, wherein each gear of the femoral gear and the tibial gear is substantially semi-circular in shape with linear portions that mesh with each other in the upright position and curved portions that mesh with each other during rotation, wherein the femoral gear includes two sets of teeth positioned on lateral sides of the knee apparatus, the tibial gear includes two sets of teeth positioned on the lateral sides of the knee apparatus, and corresponding femoral and tibial teeth on the lateral sides of the knee apparatus mesh with each other;

an anterior hard-stop that prevents anterior rotation of the femoral gear or the tibial gear when the femoral gear and the tibial gear are in the upright position, wherein the anterior hard-stop includes:
an anterior femoral stop extending downwardly along the femoral gear, and
an anterior tibial stop extending upwardly along the tibial gear, wherein the femoral stop prevents anterior rotation of the tibial gear when the femoral stop and the tibial stop abut each other, wherein the femoral stop and the tibial stop abut each other in the upright position;

at least two ligament links, each of the at least two ligament links having a first end secured on the femoral gear and a second end secured to the tibial gear, wherein each of the at least two ligament links has a biased force that facilitates flexion-extension of the femoral gear and the tibial gear relative to each other, wherein the at least two ligament links operate via a cross-linked four-bar spring mechanism that mimics an ACL and a PCL of a healthy knee, wherein each of the at least two ligament links includes:
a first ACL link secured to the femoral gear in a posterior position and secured to the tibial gear in an anterior position, such that the first ACL link extends in a posterior-to-anterior direction in the upright position of the femoral and tibial gears, wherein the first ACL link is disposed on a lateral outer surface of a first set of corresponding teeth of the femoral and tibial gears,
a second ACL link secured to the femoral gear in a posterior position and secured to the tibial gear in an anterior position, such that the second ACL link extends in a posterior-to-anterior direction in the upright position of the femoral and tibial gears, wherein the second ACL link is disposed on a lateral inner surface of a second set of corresponding teeth of the femoral and tibial gears,
a first PCL link secured to the femoral gear in an anterior position and secured to the tibial gear in a posterior position, such that the first PCL link extends in an anterior-to-posterior direction in the upright position of the femoral and tibial gears, wherein the first PCL link is disposed on a lateral outer surface of the second set of corresponding teeth of the femoral and tibial gears, and
a second PCL link secured to the femoral gear in an anterior position and secured to the tibial gear in a posterior position, such that the second PCL link extends in an anterior-to-posterior direction in the upright position of the femoral and tibial gears, wherein the second PCL link is disposed on a lateral inner surface of the first set of corresponding teeth of the femoral and tibial gears.

\* \* \* \* \*